US012753382B2

(12) United States Patent
Kim et al.

(10) Patent No.: US 12,753,382 B2
(45) Date of Patent: Oct. 6, 2026

(54) O-ACETYL HOMOSERINE-PRODUCING MICROORGANISM AND METHOD FOR PRODUCING O-ACETYL HOMOSERINE OR L-METHIONINE USING SAME

(71) Applicant: CJ CHEILJEDANG CORPORATION, Seoul (KR)

(72) Inventors: Ju Eun Kim, Seoul (KR); Ye-Eun Kim, Seoul (KR); Jaemin Lee, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 171 days.

(21) Appl. No.: 18/851,666

(22) PCT Filed: Jan. 6, 2023

(86) PCT No.: PCT/KR2023/000278

§ 371 (c)(1),
(2) Date: Sep. 26, 2024

(87) PCT Pub. No.: WO2023/191264

PCT Pub. Date: Oct. 5, 2023

(65) Prior Publication Data

US 2025/0361478 A1 Nov. 27, 2025

(30) Foreign Application Priority Data

Mar. 28, 2022 (KR) ........................ 10-2022-0038130

(51) Int. Cl.
*C12N 1/20* (2026.01)
*C12N 9/10* (2006.01)
*C12N 15/77* (2006.01)
*C12P 13/06* (2006.01)
*C12P 13/12* (2006.01)
*C12R 1/28* (2006.01)

(52) U.S. Cl.
CPC ............. *C12N 1/20* (2013.01); *C12N 9/1029* (2013.01); *C12N 15/77* (2013.01); *C12P 13/06* (2013.01); *C12P 13/12* (2013.01); *C12R 2001/28* (2021.05); *C12Y 203/01001* (2013.01)

(58) Field of Classification Search
None
See application file for complete search history.

(56) References Cited

FOREIGN PATENT DOCUMENTS

| | | | |
|---|---|---|---|
| KR | 10-2008-0102123 | A | 11/2008 |
| KR | 10-2015-0140507 | A | 12/2015 |
| KR | 10-2016-0000098 | A | 1/2016 |
| KR | 10-1641770 | B1 | 7/2016 |
| KR | 10-2018-0010382 | A | 1/2018 |
| KR | 10-1825777 | B1 | 2/2018 |
| KR | 10-2182497 | B1 | 11/2020 |
| KR | 10-2020-0136813 | A | 12/2020 |
| WO | 01/00804 | A2 | 1/2001 |
| WO | 02-081705 | A2 | 10/2002 |
| WO | 2008/013432 | A1 | 1/2008 |

OTHER PUBLICATIONS

International Search Report issued in corresponding International Patent Application No. PCT/KR2023/000278 dated Apr. 7, 2023.
NCBI, GenBank Accession No. WP_011014038.1, "GNAT family N-acetyltransferase [Corynebacteriu glutamicum]", May 15, 2021, 1 page.
Li et al., "O-acetyl-L-homoserine production enhanced by pathway strengthening and acetate supplementation in Corynebacterium glutamicum", Biotechnology for Biofuels and Bioproducts, vol. 15, No. 27, 2022, pp. 1-9.
Nguyen et al., "Elimination of polyamine N-acetylation and regulatory engineering improved putrescine production by Corynebacterium glutamicum", Journal of Biotechnology, vol. 201, 2015, pp. 75-85.
Extended European Search Report issued in corresponding European Patent Application No. 23781126.0, dated Jun. 2, 2025.
Le et al., "The Vibrio cholerae SpeG Spermidine/Spermine N-Acetyltransferase Allosteric Loop and b6-b7 Structural Elements Are Critical for Kinetic Activity", Molecular Biosciences, vol. 8, Article 645768, Apr. 2021, pp. 1-16.
Nguyen et al., "Fermentative Production of the Diamine Putrescine: System Metabolic Engineering of Corynebacterium Glutamicum", Metabolites, vol. 5, 2015, pp. 211-231.
Office Action issued in corresponding Japanese Patent Application No. 2024-558006, dated Oct. 7, 2025.

*Primary Examiner* — Brian Gangle
(74) *Attorney, Agent, or Firm* — Morgan, Lewis & Bockius LLP

(57) ABSTRACT

Provided are a microorganism in which activity of a GNAT family N-acetyltransferase protein is weakened; a method for producing O-acetyl homoserine and L-methionine using the same; a composition for producing O-acetyl homoserine, the composition including the microorganism; and use of the microorganism for producing O-acetyl homoserine or L-methionine.

9 Claims, No Drawings

Specification includes a Sequence Listing.

SEQUENCE LISTING

```
Sequence total quantity: 28
SEQ ID NO: 1              moltype = AA  length = 179
FEATURE                   Location/Qualifiers
source                    1..179
                          mol_type = protein
                          organism = Corynebacterium glutamicum
SEQUENCE: 1
MVERDFTIRP IREGDFPQVR DIYELGLETG HATYETSGPT WDQFSQSKIM DTVMVAVENN  60
DPDFILGWVS AAPISSRQVF HGVVEDSIYI HPQGQGRGIG GALLDALITY CESNGIWSIH  120
SWIFPENLGS AKLHESKGFV KVGTMHQMAR MPYGEMEGQW RDCDLWECLL SVPEQAQSS   179

SEQ ID NO: 2              moltype = DNA  length = 540
FEATURE                   Location/Qualifiers
source                    1..540
                          mol_type = genomic DNA
                          organism = Corynebacterium glutamicum
SEQUENCE: 2
atggttgaaa gagacttcac tatccgacca atccgcgagg gtgatttccc tcaggtgagg  60
gacatctacg aattgggcct ggagacggga catgcgactt atgagacttc tggtcccacg  120
tgggaccagt tctcccaatc taaaatcatg gataccgtca tggtggcggt agaaaacaac  180
gacccggact tcatcctcgg atgggtgtct gctgctccaa tttcaagccg acaggttttc  240
catggagtgg tggaagattc catctatatc cacccccagg gccaaggccg aggaatcggc  300
ggcgctttgc tcgacgccct tatcacctac tgcgaaagca acggcatctg gtcgatccac  360
tcctggatct tcccggaaaa cctcggttct gcgaaactgc atgaatcgaa gggcttcgtg  420
aaggtgggca ccatgcacca aatggcaagg atgccctacg gcgagatgga aggacaatgg  480
cgcgattgtg atctgtggga gtgcctctta tccgttccag agcaagctca aagttcctaa  540

SEQ ID NO: 3              moltype = DNA  length = 40
FEATURE                   Location/Qualifiers
misc_feature              1..40
                          note = 0959 _del up F
source                    1..40
                          mol_type = other DNA
                          organism = synthetic construct
SEQUENCE: 3
tgaattcgag ctcggtaccc atccacagac ggtcatcgtg                        40

SEQ ID NO: 4              moltype = DNA  length = 33
FEATURE                   Location/Qualifiers
misc_feature              1..33
                          note = 0959 _del up R
source                    1..33
                          mol_type = other DNA
                          organism = synthetic construct
SEQUENCE: 4
tttggtggat atccatgcac gcaattgtcc tgg                               33

SEQ ID NO: 5              moltype = DNA  length = 33
FEATURE                   Location/Qualifiers
misc_feature              1..33
                          note = 0959 _del down F
source                    1..33
                          mol_type = other DNA
                          organism = synthetic construct
SEQUENCE: 5
gtgcatggat atccaccaaa tggcaaggat gcc                               33

SEQ ID NO: 6              moltype = DNA  length = 40
FEATURE                   Location/Qualifiers
misc_feature              1..40
                          note = 0959 _del down R
source                    1..40
                          mol_type = other DNA
                          organism = synthetic construct
SEQUENCE: 6
gtcgactcta gaggatcccc gcagagatcg ttgattcaat                        40
```

```
SEQ ID NO: 7            moltype = DNA  length = 5803
FEATURE                 Location/Qualifiers
misc_feature            1..5803
                        note = pDCM2
source                  1..5803
                        mol_type = other DNA
                        organism = synthetic construct
SEQUENCE: 7
gttcgcttgc tgtccataaa accgcccagt ctagctatcg ccatgtaagc ccactgcaag  60
ctacctgctt tctctttgcg cttgcgtttt cccttgtcca gatagcccag tagctgacat  120
tcatccgggg tcagcaccgt ttctgcggac tggctttcta cgtgttccgc ttcctttagc  180
agcccttgcg ccctgagtgc ttgcggcagc gtgaagctag cttttatcgc cattcgccat  240
tcaggctgcg caactgttgg gaagggcgat cggtgcgggc ctcttcgcta ttacgccagc  300
tggcgaaagg gggatgtgct gcaaggcgat taagttgggt aacgccaggg ttttcccagt  360
cacgacgttg taaaacgacg gccagtgaat tcgagctcgg tacccgggga tcctctagag  420
tcgacctgca ggcatgcaag cttggcgtaa tcatggtcat agctgtttcc tgtgtgaaat  480
tgttatccgc tcacaattcc acacaacata cgagccggaa gcataaagtg taaagcctgg  540
ggtgcctaat gagtgagcta actcacatta attgcgttgc gctcactgcc cgctttccag  600
tcgggaaacc tgtcgtgcca gctgcattaa tgaatcggcc aacgcgcggg gagaggcggt  660
ttgcgtattg ggcgctcttc cgcttcctcg ctcactgact cgctgcgctc ggtcgttcgg  720
ctgcggcgag cggtatcagc tcactcaaag gcggtaatac ggttatccac agaatcaggg  780
gataacgcag gaaagaacat gtgagcaaaa ggccagcaaa aggccaggaa ccgtaaaaag  840
gccgcgttgc tggcgttttt ccataggctc cgcccccctg acgagcatca caaaaatcga  900
cgctcaagtc agaggtggcg aaacccgaca ggactataaa gataccaggc gtttccccct  960
ggaagctccc tcgtgcgctc tcctgttccg accctgccgc ttaccggata cctgtccgcc  1020
tttctccctt cgggaagcgt ggcgctttct caatgctcac gctgtaggta tctcagttcg  1080
gtgtaggtcg ttcgctccaa gctgggctgt gtgcacgaac cccccgttca gcccgaccgc  1140
tgcgccttat ccggtaacta tcgtcttgag tccaacccgg taagacacga cttatcgcca  1200
ctggcagcag ccactggtaa caggattagc agagcgaggt atgtaggcgg tgctacagag  1260
ttcttgaagt ggtggcctaa ctacggctac actagaagga cagtatttgg tatctgcgct  1320
ctgctgaagc cagttacctt cggaaaaaga gttggtagct cttgatccgg caaacaaacc  1380
accgctggta gcggtggttt ttttgtttgc aagcagcaga ttacgcgcag aaaaaaagga  1440
tctcaagaag atcctttgat cttttctacg gggtctgacg ctcagtggaa cgaaaactca  1500
cgttaaggga ttttggtcat gagattatca aaaaggatct tcacctagat ccttttgggg  1560
tgggcgaaga actccagcat gagatccccg cgctggagga tcatccagcc ctgatagaaa  1620
cagaagccac tggagcacct caaaaacacc atcatacact aaatcagtaa gttggcagca  1680
tcacccgacg cactttgcgc cgaataaata cctgtgacgg aagatcactt cgcagaataa  1740
ataaatcctg gtgtccctgt tgataccggg aagccctggg ccaacttttg gcgaaaatga  1800
gacgttgatc ggcacgtaag aggttccaac tttcaccata atgaaataag atcactaccg  1860
ggcgtatttt ttgagttatc gagattttca ggagctgata gaaacagaag ccactggagc  1920
acctcaaaaa caccatcata cactaaatca gtaagttggc agcatcaccc gacgcacttt  1980
gcgccgaata aatacctgtg acggaagatc acttcgcaga ataaataaat cctggtgtcc  2040
ctgttgatac cgggaagccc tgggccaact tttggcgaaa atgagacgtt gatcggcacg  2100
taagaggttc caactttcac cataatgaaa taagatcact accgggcgta ttttttgagt  2160
tatcgagatt ttcaggagct ctttggcatc gtctctcgcc tgtcccctca gttcagtaat  2220
ttcctgcatt tgcctgtttc cagtcggtag atattccaca aaacagcagg gaagcagcgc  2280
ttttccgctg cataaccctg cttcggggtc attatagcga tttttcggt atatccatcc  2340
tttttcgcac gatatacagg attttgccaa agggttcgtg tagactttcc ttggtgtatc  2400
caacggcgtc agccgggcag gataggtgaa gtaggcccac ccgcgagcgg gtgttccttc  2460
ttcactgtcc cttattcgca cctggcggtg ctcaacggga atcctgctct gcgaggctgg  2520
ccggctaccg ccggcgtaac agatgagggc aagcggatgg ctgatgaaac caagccaacc  2580
aggaagggca gcccacctat caaggtgtac tgccttccag acgaacgaag agcgattgag  2640
gaaaaggcgg cggcggccgg catgagcctg tcggcctacc tgctggccgt cggccagggc  2700
tacaaaatca cgggcgtcgt ggactatgag cacgtccgcg agggcgtccc ggaaaacgat  2760
tccgaagccc aacctttcat agaaggcggc ggtggaatcg aaatctcgtg atggcaggtt  2820
gggcgtcgct tggtcggtca tttcgaaaaa ggttaggaat acggttagcc atttgcctgc  2880
ttttatatag ttcantatgg gattcacctt tatgttgata agaaataaaa gaaaatgcca  2940
ataggatatc ggcattttct tttgcgtttt tatttgttaa ctgttaattg tccttgttca  3000
aggatgctgt ctttgacaac agatgttttc ttgcctttga tgttcagcag gaagctcggc  3060
gcaaacgttg attgtttgtc tgcgtagaat cctctgtttg tcatatagct tgtaatcacg  3120
acattgtttc ctttcgcttg aggtacagcg aagtgtgagt aagtaaaggt tacatcgtta  3180
ggcggatcaa gatccatttt taacacaagg ccagttttgt tcagcggctt gtatgggcca  3240
gttaaagaat tagaaacata accaagcatg taaatatcgt tagacgtaat gccgtcaatc  3300
gtcatttttg atccgcggga gtcagtgaac aggtaccatt tgccgttcat tttaaagacg  3360
ttcgcgcgtt caatttcatc tgttactgtg ttagatgcaa tcagcggttt catcactttt  3420
ttcagtgtgt aatcatcgtt tagctcaatc ataccgagag cgccgtttgc taactcagcc  3480
gtgcgttttt tatcgctttg cagaagtttt tgactttctt gacggaagaa tgatgtgctt  3540
ttgccatagt atgctttgtt aaataaagat tcttcgcctt ggtagccatc ttcagttcca  3600
gtgtttgctt caaatactaa gtatttgtgg cctttatctt ctacgtagtg aggatctctc  3660
agcgtatggt tgtcgcctga gctgtagttg ccttcatcga tgaactgctg tacattttga  3720
tacgtttttc cgtcaccgtc aaagattgat ttataatcct ctacaccgtt gatgttcaaa  3780
gagctgtctg atgctgatac gttaacttgt gcagttgtca gtgtttgttt gccgtaatgt  3840
ttaccggaga aatcagtgta gaataaacgg atttttccgt cagatgtaaa tgtggctgaa  3900
cctgaccatt cttgtgtttg gtcttttagg atagaatcat ttgcatcgaa tttgtcgctg  3960
tctttaaaga cgcggccagc gtttttccag ctgtcaatag aagtttcgcc gactttttga  4020
tagaacatgt aaatcgatgt gtcatccgca tttttaggat ctccggctaa tgcaaagacg  4080
atgtggtagc cgtgatagtt tgcgacagtg ccgtcagcgt tttgtaatgg ccagctgtcc  4140
caaacgtcca ggccttttgc agaagagata tttttaattg tggacgaatc aaattcagaa  4200
```

```
acttgatatt tttcattttt ttgctgttca gggatttgca gcatatcatg gcgtgtaata  4260
tgggaaatgc cgtatgtttc cttatatggc ttttggttcg tttctttcgc aaacgcttga  4320
gttgcgcctc ctgccagcag tgcggtagta aaggttaata ctgttgcttg ttttgcaaac  4380
tttttgatgt tcatcgttca tgtctccttt tttatgtact gtgttagcgg tctgcttctt  4440
ccagccctcc tgtttgaaga tggcaagtta gttacgcaca ataaaaaaag acctaaaata  4500
tgtaaggggt gacgccaaag tatacacttt gccctttaca cattttaggt cttgcctgct  4560
ttatcagtaa caaacccgcg cgatttactt ttcgacctca ttctattaga ctctcgtttg  4620
gattgcaact ggtctatttt cctcttttgt ttgatagaaa atcataaaag gatttgcaga  4680
ctacgggcct aaagaactaa aaaatctatc tgtttctttt cattctctgt atttttata  4740
gtttctgttg catgggcata aagttgcctt tttaatcaca attcagaaaa tatcataata  4800
tctcatttca ctaaataata gtgaacggca ggtatatgtg atgggttaaa aaggatcacc  4860
ccagagtccc gctcagaaga actcgtcaag aaggcgatag aaggcgatgc gctgcgaatc  4920
gggagcggcg ataccgtaaa gcacgaggaa gcggtcagcc cattcgccgc caagctcttc  4980
agcaatatca cgggtagcca acgctatgtc ctgatagcgg tccgccacac ccagccggcc  5040
acagtcgatg aatccagaaa agcggccatt ttccaccatg atattcggca agcaggcatc  5100
gccatgggtc acgacgagat cctcgccgtc gggcatccgc gccttgagcc tggcgaacag  5160
ttcggctggc gcgagcccct gatgctcttc gtccagatca tcctgatcga caagaccggc  5220
ttccatccga gtacgtgctc gctcgatgcg atgtttcgct tggtggtcga atgggcaggt  5280
agccggatca agcgtatgca gccgccgcat tgcatcagcc atgatggata ctttctcggc  5340
aggagcaagg tgagatgaca ggagatcctg ccccggcact tcgcccaata gcagccagtc  5400
ccttcccgct tcagtgacaa cgtcgagaca gctgcgcaag gaacgcccgt cgtggccagc  5460
cacgatagcc gcgctgcctc gtcttggagt tcattcaggg caccggacag gtcggtcttg  5520
acaaaaagaa ccgggcgccc ctgcgctgac agccggaaca cggcggcatc agagcagccg  5580
attgtctgtt gtgcccagtc atagccgaat agcctctcca cccaagcggc cggagaacct  5640
gcgtgcaatc catcttgttc aatcatgcga aacgatcctc atcctgtctc ttgatcagat  5700
cttgatcccc tgcgccatca gatccttggc ggcaagaaag ccatccagtt tactttgcag  5760
ggcttcccaa ccttaccaga gggcgcccca gctggcaatt ccg                   5803

SEQ ID NO: 8             moltype = DNA  length = 25
FEATURE                  Location/Qualifiers
misc_feature             1..25
                         note = 0959 _del F
source                   1..25
                         mol_type = other DNA
                         organism = synthetic construct
SEQUENCE: 8
gtgaaaaaac actggcaaaa caagc                                        25

SEQ ID NO: 9             moltype = DNA  length = 25
FEATURE                  Location/Qualifiers
misc_feature             1..25
                         note = 0959 _del R
source                   1..25
                         mol_type = other DNA
                         organism = synthetic construct
SEQUENCE: 9
ataagaggca ctcccacaga tcaca                                        25

SEQ ID NO: 10            moltype = AA  length = 418
FEATURE                  Location/Qualifiers
REGION                   1..418
                         note = YjeH F351L
source                   1..418
                         mol_type = protein
                         organism = synthetic construct
SEQUENCE: 10
MSGLKQELGL AQGIGLLSTS LLGTGVFAVP ALAALVAGNN SLWAWPVLII LVFPIAIVFA  60
ILGRHYPSAG GVAHFVGMAF GSRLERVTGW LFLSVIPVGL PAALQIAAGF GQAMFGWHSW  120
QLLLAELGTL ALVWYIGTRG ASSSANLQTV IAGLIVALIV AIWWAGDIKP ANIPFPAPGN  180
IELTGLFAAL SVMFWCFVGL EAFAHLASEF KNPERDFPRA LMIGLLLAGL VYWGCTVVVL  240
HFDAYGEKMA AAASLPKIVV QLFGVGALWI ACVIGYLACF ASLNIYIQSF ARLVWSQAQH  300
NPDHYLARLS SRHIPNNALN AVLGCCVVST LVIHALEINL DALIIYANGI LIMIYLLCML  360
AGCKLLQGRY RLLAVVGGLL CVLLLAMVGW KSLYALIMLA GLWLLLPKRK TPENGITT    418

SEQ ID NO: 11            moltype = DNA  length = 1161
FEATURE                  Location/Qualifiers
misc_feature             1..1161
                         note = Corynebacterium glutamicum metB
source                   1..1161
                         mol_type = genomic DNA
                         organism = unidentified
SEQUENCE: 11
ttgtcttttg acccaaacac ccagggtttc tccactgcat cgattcacgc tgggtatgag  60
ccagacgact actacggttc gattaacacc ccaatctatg cctccaccac cttcgcgcag  120
aacgctccaa acgaactgcg caaaggctac gagtacaccc gtgtgggcaa ccccaccatc  180
gtggcattag agcagaccgt cgcagcactc gaaggcgcaa agtatggccg cgcattctcc  240
tccggcatgg ctgcaaccga catcctgttc cgcatcatcc tcaagccggg cgatcacatc  300
gtcctcggca acgatgctta cggcggaacc taccgcctga tcgacaccgt attcaccgca  360
tggggcgtcg aatacaccgt tgttgatacc tccgtcgtgg aagaggtcaa ggcagcgatc  420
```

```
aaggacaaca ccaagctgat ctgggtggaa accccaacca acccagcact tggcatcacc  480
gacatcgaag cagtagcaaa gctcaccgaa ggcaccaacg ccaagctggt tgttgacaac  540
accttcgcat ccccatacct gcagcagcca ctaaaactcg gcgcacacgc agtcctgcac  600
tccaccacca agtacatcgg aggacactcc gacgttgttg gcggccttgt ggttaccaac  660
gaccaggaaa tggacgaaga actgctgttc atgcagggcg gcatcggacc gatcccatca  720
gttttcgatg catacctgac cgcccgtggc ctcaagaccc ttgcagtgcg catggatcgc  780
cactgcgaca acgcagaaaa gatcgcggaa ttcctggact cccgcccaga ggtctccacc  840
gtgctctacc caggtctgaa gaaccaccca ggccacgaag tcgcagcgaa gcagatgaag  900
cgcttcggcg gcatgatctc cgtccgtttc gcaggcggcg aagaagcagc taagaagttc  960
tgtacctcca ccaaactgat ctgtctggcc gagtccctcg gtggcgtgga atccctcctg  1020
gagcacccag caaccatgac ccaccagtca gctgccggct ctcagctcga ggttccccgc  1080
gacctcgtgc gcatctccat tggtattgaa gacattgaag acctgctcgc agatgtcgag  1140
caggccctca ataaccttta g                                           1161

SEQ ID NO: 12          moltype = DNA  length = 18
FEATURE                Location/Qualifiers
misc_feature           1..18
                       note = metB_N_del F
source                 1..18
                       mol_type = other DNA
                       organism = synthetic construct
SEQUENCE: 12
ggcttcggag ttggagcg                                               18

SEQ ID NO: 13          moltype = DNA  length = 40
FEATURE                Location/Qualifiers
misc_feature           1..40
                       note = metB_N_del R
source                 1..40
                       mol_type = other DNA
                       organism = synthetic construct
SEQUENCE: 13
gccaaatagt ttcccggggg tagatcaact cctgtaatca                       40

SEQ ID NO: 14          moltype = DNA  length = 40
FEATURE                Location/Qualifiers
misc_feature           1..40
                       note = metB_C_del F
source                 1..40
                       mol_type = other DNA
                       organism = synthetic construct
SEQUENCE: 14
caggagttga tctacccccg ggaaactatt tggcggcaag                       40

SEQ ID NO: 15          moltype = DNA  length = 19
FEATURE                Location/Qualifiers
misc_feature           1..19
                       note = metB_C_del R
source                 1..19
                       mol_type = other DNA
                       organism = synthetic construct
SEQUENCE: 15
tcgcgtctgg gtgcgcatc                                              19

SEQ ID NO: 16          moltype = DNA  length = 1314
FEATURE                Location/Qualifiers
misc_feature           1..1314
                       note = Corynebacterium glutamicum metY
source                 1..1314
                       mol_type = other DNA
                       organism = synthetic construct
SEQUENCE: 16
atgccaaagt acgacaattc caatgctgac cagtggggct ttgaaacccg ctccattcac  60
gcaggccagt cagtagacgc acagaccagc gcacgaaacc ttccgatcta ccaatccacc  120
gctttcgtgt tcgactccgc tgagcacgcc aagcagcgtt tcgcacttga ggatctaggc  180
cctgtttact cccgcctcac caacccaacc gttgaggctt tggaaaaccg catcgcttcc  240
ctcgaaggtg gcgtccacgc tgtagcgttc tcctccggac aggccgcaac caccaacgcc  300
attttgaacc tggcaggagc gggcgaccac atcgtcacct ccccacgcct ctacggtggc  360
accgagactc tattccttat cactcttaac cgcctgggta tcgatgtttc cttcgtggaa  420
aaccccgacg accctgagtc ctggcaggca gccgttcagc caaacaccaa agcattcttc  480
ggcgagactt tcgccaaccc acaggcagac gtcctggata ttcctgcggt ggctgaagtt  540
gcgcaccgca acagcgttcc actgatcatc gacaacacca tcgctaccgc agcgctcgtg  600
cgcccgctcg agctcggcgc agacgttgtc gtcgcttccc tcaccaagtt ctacaccggc  660
aacggctccg gactgggcgg cgtgcttatc gacggcggaa agttcgattg gactgtcgaa  720
aaggatggaa agccagtatt cccctacttc gtcactccag atgctgctta ccacggattg  780
aagtacgcag accttggtgc accagccttc ggcctcaagg ttcgcgttgg ccttctacgc  840
gacaccggct ccaccctctc cgcattcaac gcatgggctg cagtccaggg catcgacacc  900
ctttccctgc gcctggagcg ccacaacgaa aacgccatca aggttgcaga attcctcaac  960
aaccacgaga aggtggaaaa ggttaacttc gcaggcctga aggattcccc ttggtacgca  1020
```

```
accaaggaaa agcttggcct gaagtacacc ggctccgttc tcaccttcga gatcaagggc  1080
ggcaaggatg aggcttgggc atttatcgac gccctgaagc tacactccaa ccttgcaaac  1140
atcggcgatg ttcgctccct cgttgttcac ccagcaacca ccacccattc acagtccgac  1200
gaagctggcc tggcacgcgc gggcgttacc cagtccaccg tccgcctgtc cgttggcatc  1260
gagaccattg atgatatcat cgctgacctc gaaggcggct ttgctgcaat ctag        1314

SEQ ID NO: 17          moltype = DNA  length = 18
FEATURE                Location/Qualifiers
misc_feature           1..18
                       note = metY_N_del F
source                 1..18
                       mol_type = other DNA
                       organism = synthetic construct
SEQUENCE: 17
ccaaagacaa ggagacca                                                18

SEQ ID NO: 18          moltype = DNA  length = 40
FEATURE                Location/Qualifiers
misc_feature           1..40
                       note = metY_N_del R
source                 1..40
                       mol_type = other DNA
                       organism = synthetic construct
SEQUENCE: 18
agtctattta aagcccgggt tggaggtcct taagagtttt                        40

SEQ ID NO: 19          moltype = DNA  length = 40
FEATURE                Location/Qualifiers
misc_feature           1..40
                       note = metY_C_del F
source                 1..40
                       mol_type = other DNA
                       organism = synthetic construct
SEQUENCE: 19
taaggacctc caacccgggc tttaaataga ctcaccccag                        40

SEQ ID NO: 20          moltype = DNA  length = 18
FEATURE                Location/Qualifiers
misc_feature           1..18
                       note = metY_C_del R
source                 1..18
                       mol_type = other DNA
                       organism = synthetic construct
SEQUENCE: 20
atgccgagtg cgtcgagg                                                18

SEQ ID NO: 21          moltype = DNA  length = 1266
FEATURE                Location/Qualifiers
misc_feature           1..1266
                       note = Corynebacterium glutamicum lysC
source                 1..1266
                       mol_type = genomic DNA
                       organism = unidentified
SEQUENCE: 21
gtggccctgg tcgtacagaa atatggcggt tcctcgcttg agagtgcgga acgcattaga  60
aacgtcgctg aacggatcgt tgccaccaag aaggctggaa atgatgtcgt ggttgtctgc  120
tccgcaatgg gagacaccac ggatgaactt ctagaacttg cagcggcagt gaatcccgtt  180
ccgccagctc gtgaaatgga tatgctcctg actgctggtg agcgtatttc taacgctctc  240
gtcgccatgg ctattgagtc ccttggcgca gaagcccaat ctttcacggg ctctcaggct  300
ggtgtgctca ccaccgagcg ccacggaaac gcacgcattg ttgatgtcac tccaggtcgt  360
gtgcgtgaag cactcgatga gggcaagatc tgcattgttg ctggtttcca gggtgttaat  420
aaagaaaccc gcgatgtcac cacgttgggt cgtggtggtt ctgacaccac tgcagttgcg  480
ttggcagctg ctttgaacgc tgatgtgtgt gagatttact cggacgttga cggtgtgtat  540
accgctgacc cgcgcatcgt tcctaatgca cagaagctgg aaaagctcag cttcgaagaa  600
atgctggaac ttgctgctgt tggctccaag attttggtgc tgcgcagtgt tgaatacgct  660
cgtgcattca atgtgccact tcgcgtacgc tcgtcttata gtaatgatcc cggcactttg  720
attgccggct ctatggagga tattcctgtg gaagaagcag tccttaccgg tgtcgcaacc  780
gacaagtccg aagccaaagt aaccgttctg ggtatttccg ataagccagg cgaggctgcg  840
aaggttttcc gtgcgttggc tgatgcagaa atcaacattg acatggttct gcagaacgtc  900
tcttctgtag aagacggcac caccgacatc accttcacct gccctcgttc cgacggccgc  960
cgcgcgatgg agatcttgaa gaagcttcag gttcagggca actggaccaa tgtgctttac  1020
gacgaccagg tcggcaaagt ctccctcgtg ggtgctggca tgaagtctca cccaggtgtt  1080
accgcagagt tcatggaagc tctgcgcgat gtcaacgtga acatcgaatt gatttccacc  1140
tctgagattc gtatttccgt gctgatccgt gaagatgatc tggatgctgc tgcacgtgca  1200
ttgcatgagc agttccagct gggcggcgaa gacgaagccg tcgtttatgc aggcaccgga  1260
cgctaa                                                             1266

SEQ ID NO: 22          moltype = DNA  length = 19
FEATURE                Location/Qualifiers
```

```
misc_feature           1..19
                       note = lysC_L377K_5 F
source                 1..19
                       mol_type = other DNA
                       organism = synthetic construct
SEQUENCE: 22
cagaagctgg aaaagctca                                           19

SEQ ID NO: 23          moltype = DNA  length = 40
FEATURE                Location/Qualifiers
misc_feature           1..40
                       note = lysC_L377K_5 R
source                 1..40
                       mol_type = other DNA
                       organism = synthetic construct
SEQUENCE: 23
atctcagagg tggaaatctt ttcgatgttc acgttgacat                    40

SEQ ID NO: 24          moltype = DNA  length = 40
FEATURE                Location/Qualifiers
misc_feature           1..40
                       note = lysC_L377K_3 F
source                 1..40
                       mol_type = other DNA
                       organism = synthetic construct
SEQUENCE: 24
tgtcaacgtg aacatcgaaa agatttccac ctctgagatt                    40

SEQ ID NO: 25          moltype = DNA  length = 19
FEATURE                Location/Qualifiers
misc_feature           1..19
                       note = lysC_L377K_3 R
source                 1..19
                       mol_type = other DNA
                       organism = synthetic construct
SEQUENCE: 25
tccttgtcgg aagggttca                                           19

SEQ ID NO: 26          moltype = DNA  length = 1134
FEATURE                Location/Qualifiers
misc_feature           1..1134
                       note = Corynebacterium glutamicum metX
source                 1..1134
                       mol_type = other DNA
                       organism = synthetic construct
SEQUENCE: 26
atgcccaccc tcgcgccttc aggtcaactt gaaatccaag cgatcggtga tgtctccacc  60
gaagccggag caatcattac aaacgctgaa atcgcctatc accgctgggg tgaataccgc  120
gtagataaag aaggacgcag caatgtcgtt ctcatcgaac acgccctcac tggagattcc  180
aacgcagccg attggtgggc tgacttgctc ggtcccggca aagccatcaa cactgatatt  240
tactgcgtga tctgtaccaa cgtcatcggt ggttgcaacg gttccaccgg acctggctcc  300
atgcatccag atggaaattt ctggggtaat cgcttccccg ccacgtccat tcgtgatcag  360
gtaaacgccg aaaaacaatt cctcgacgca ctcggcatca ccacggtcgc cgcagtactt  420
ggtggttcca tgggtggtgc ccgcacccta gagtgggccg caatgtaccc agaaactgtt  480
ggcgcagctg ctgttcttgc agtttctgca cgcgccagcg cctggcaaat cggcattcaa  540
tccgcccaaa ttaaggcgat tgaaaacgac caccactggc acgaaggcaa ctactacgaa  600
tccggctgca acccagccac cggactcggc gccgcccgac gcatcgccca cctcacctac  660
cgtggcgaac tagaaatcga cgaacgcttc ggcaccaaag cccaaaagaa cgaaaaccca  720
ctcggtccct accgcaagcc cgaccagcgc ttcgccgtgg aatcctactt ggactaccaa  780
gcagacaagc tagtacagcg tttcgacgcc ggctcctacg tcttgctcac cgacgccctc  840
aaccgccacg acattggtcg cgaccgcgga ggcctcaaca aggcactcga atccatcaaa  900
gttccagtcc ttgtcgcagg cgtagatacc gatattttgt acccctacca ccagcaagaa  960
cacctctcca gaaacctggg aaatctactg gcaatggcaa aaatcgtatc cctgtcggc  1020
cacgatgctt tcctcaccga aagccgccaa atggatcgca tcgtgaggaa cttcttcagc  1080
ctcatctccc cagacgaaga caacccttcg acctacatcg agttctacat ctaa        1134

SEQ ID NO: 27          moltype = DNA  length = 28
FEATURE                Location/Qualifiers
misc_feature           1..28
                       note = metX F
source                 1..28
                       mol_type = other DNA
                       organism = synthetic construct
SEQUENCE: 27
ggatcccctc gttgttcacc cagcaacc                                 28

SEQ ID NO: 28          moltype = DNA  length = 30
FEATURE                Location/Qualifiers
misc_feature           1..30
```

-continued

```
                        note = metX R
source                  1..30
                        mol_type = other DNA
                        organism = synthetic construct
SEQUENCE: 28
ggatcccaaa gtcacaacta cttatgttag                        30
```

O-ACETYL HOMOSERINE-PRODUCING MICROORGANISM AND METHOD FOR PRODUCING O-ACETYL HOMOSERINE OR L-METHIONINE USING SAME

A computer readable xml file, entitled "133660-04-9070-US_Sequence_Listing_ST26.xml," created on or about Sep. 25, 2024, with a file size of 47,585 bytes contains the sequence listing for this application and is hereby incorporated by reference in its entirety.

TECHNICAL FIELD

The present disclosure relates to a microorganism in which activity of a GNAT family N-acetyltransferase protein is weakened; a method for producing O-acetyl homoserine and L-methionine using the same; a composition for producing O-acetyl homoserine, the composition including the microorganism; and use of the microorganism for producing O-acetyl homoserine or L-methionine.

BACKGROUND ART

O-Acetyl homoserine acts as a precursor of methionine, which is one of the essential amino acids in the living body. Methionine, which is one of the essential amino acids in the living body, has been widely used in feeds and food additives as well as in infusion solutions and as a raw material for medicinal products.

Methionine is produced through biological or chemical synthesis. In this regard, a two-step process of producing L-methionine by an enzymatic conversion reaction from an L-methionine precursor produced through fermentation was disclosed (International Publication No. WO2008/013432).

In the above two-step process, O-succinyl homoserine and O-acetyl homoserine may be used as the methionine precursor. Accordingly, it is important to produce O-acetyl homoserine in a high yield for large-scale cost-effective production of methionine.

DISCLOSURE

Technical Problem

The present inventors have developed a microorganism of the genus *Corynebacterium* producing O-acetyl homoserine, and a method for producing O-acetyl homoserine or L-methionine using the same, thereby completing the present disclosure.

Technical Solution

An object of the present disclosure is to provide a microorganism of the genus *Corynebacterium* with O-acetyl homoserine-producing ability, in which activity of a GNAT family N-acetyltransferase protein is weakened.

Another object of the present disclosure is to provide a method for producing O-acetyl homoserine, the method including the step of culturing the microorganism in a medium.

Still another object of the present disclosure is to provide a method for producing L-methionine, the method including the step of culturing the microorganism in a medium.

Still another object of the present disclosure is to provide a composition for producing O-acetyl homoserine, the composition including the microorganism.

Still another object of the present disclosure is to provide use of the microorganism of the present disclosure for producing O-acetyl homoserine or L-methionine.

Advantageous Effects

A microorganism producing O-acetyl homoserine of the present disclosure is able to O-acetyl homoserine in an environmentally friendly and highly efficient manner, as compared to chemical synthesis. In addition, the produced O-acetyl homoserine may be used as a precursor for the synthesis of methionine and acetic acid by O-acetyl homoserine sulfhydrylase, thereby achieving highly efficient bioconversion of L-methionine, and the converted L-methionine may be widely used in the production of animal feeds or animal feed additives as well as human food or food additives.

DETAILED DESCRIPTION OF PREFERRED EMBODIMENTS

The present disclosure will be described in detail as follows. Meanwhile, each description and embodiment disclosed in this disclosure may also be applied to other descriptions and embodiments. That is, all combinations of various elements disclosed in this disclosure fall within the scope of the present disclosure. Further, the scope of the present disclosure is not limited by the specific description described below.

Further, a number of papers and patent documents are referenced and cited throughout this specification. The disclosures of the cited papers and patent documents are incorporated herein by reference in their entirety to further clarify the level and scope of the subject matter to which the present disclosure pertains.

An aspect of the present disclosure provides a microorganism of the genus *Corynebacterium* with O-acetyl homoserine-producing ability, in which the activity of a GNAT family N-acetyltransferase protein is weakened.

As used herein, the term "GNAT family N-acetyltransferase" refers to a N-acetyltransferase belonging to the GNAT (Gcn5-Related N-Acetyltransferases) family.

Specifically, the GNAT family N-acetyltransferase is known in the art, and protein and gene sequences of the GNAT family N-acetyltransferase may be obtained from known databases, and examples thereof may include the NCBI GenBank, etc., but are not limited thereto. More specifically, the GNAT family N-acetyltransferase may have and/or may include an amino acid sequence represented by SEQ ID NO: 1, or may essentially consist of or may consist of the amino acid sequence. For example, the protein consisting of SEQ ID NO: 1 may refer to a protein inherently present in microorganisms of the genus *Corynebacterium*, which is encoded by the known NCgl0959 gene, but is not limited thereto, specifically, GNAT family N-acetyltransferase consisting of the amino acid sequence of SEQ ID NO: 1 inherently present in microorganisms of the genus *Corynebacterium*, and more specifically, GNAT family N-acetyltransferase of *Corynebacterium glutamicum* ATCC 13032, encoded by NCgl0959 gene, but is not limited thereto.

Further, the GNAT family N-acetyltransferase of the present disclosure may include the amino acid sequence represented by SEQ ID NO: 1 as well as an amino acid sequence having at least 70%, 75%, 80%, 85%, 90%, 95%, 96%, 97%, 98%, 99%, 99.5%, 99.7% or 99.9% or more homology or identity to SEQ ID NO: 1. It is also apparent that any amino acid sequence with deletion, modification, substitution, conservative substitution, or addition in part of the sequence may also be included within the scope of the present disclosure as long as the amino acid sequence has such homology or identity and has biological activity identical or corresponding to that of the GNAT family N-acetyltransferase of the present disclosure.

In the present disclosure, although being described as 'a polypeptide or protein including an amino acid sequence represented by a specific SEQ ID NO.', 'a polypeptide or protein consisting of an amino acid sequence represented by a specific SEQ ID NO.', or 'a polypeptide or protein having an amino acid sequence represented by a specific SEQ ID NO.', it is obvious that any protein having an amino acid sequence with deletion, modification, substitution, conservative substitution, or addition in part of the sequence may be used in the present disclosure as long as the protein has activity identical or corresponding to that of the polypeptide consisting of the amino acid sequence of the corresponding SEQ ID NO. For example, there are cases of having addition of a sequence which does not alter the function of the protein at the N-terminus and/or C-terminus of the amino acid sequence, a naturally occurring mutation, a silent mutation thereof, or a conservative substitution.

For example, there are cases of having addition or deletion of a sequence which does not alter the function of the GNAT family N-acetyltransferase of the present disclosure at the N-terminus, C-terminus, and/or inside the amino acid sequence, a naturally occurring mutation, a silent mutation thereof, or a conservative substitution.

As used herein, the term "conservative substitution" means substituting an amino acid with another amino acid having similar structural and/or chemical properties. Such amino acid substitution may generally occur based on similarity in the polarity, charge, solubility, hydrophobicity, hydrophilicity and/or amphipathic nature of the residue. For example, positively charged (basic) amino acids include arginine, lysine, and histidine; negatively charged (acidic) amino acids include glutamic acid and aspartate; aromatic amino acids include phenylalanine, tryptophan, and tyrosine; and hydrophobic amino acids include alanine, valine, isoleucine, leucine, methionine, phenylalanine, tyrosine, and tryptophan. Further, amino acids may be classified into amino acids with electrically charged side chains and amino acids with uncharged side chains. The amino acids with electrically charged side chains include aspartic acid, glutamic acid, lysine, arginine, and histidine, and the amino acids with uncharged side chains may be further classified into nonpolar amino acids or polar amino acids. The nonpolar amino acids include glycine, alanine, valine, leucine, isoleucine, methionine, phenylalanine, tryptophan, and proline, and polar amino acids include serine, threonine, cysteine, tyrosine, asparagine, and glutamine. Commonly, the conservative substitution may have little or no effect on the activity of produced polypeptide. Commonly, the conservative substitution may have little or no effect on the activity of protein or polypeptide.

Further, the GNAT family N-acetyltransferase may also include deletion or addition of amino acids that have minimal influence on the properties and secondary structure of the polypeptide. For example, a polypeptide may be conjugated to a signal (or leader) sequence at the N-terminus of the protein, which co-translationally or post-translationally directs transfer of the protein. The polypeptide may also be conjugated to other sequence or a linker for identification, purification, or synthesis of the polypeptide.

As used herein, the term 'homology' or 'identity' refers to a degree of similarity between two given amino acid sequences or nucleotide sequences, and may be expressed as a percentage. The terms homology and identity may often be used interchangeably with each other.

The sequence homology or identity of a conserved polynucleotide or polypeptide is determined by standard alignment algorithms, and the default gap penalty established by a program used may be used together. Substantially, homologous or identical sequences may generally hybridize under moderately or highly stringent conditions to the entirety or a part of the sequence. It is apparent that hybridization also includes hybridization of a polynucleotide with a polynucleotide including a general codon or a codon in consideration of codon degeneracy.

Whether or not any two polynucleotide or polypeptide sequences have homology, similarity, or identity may be determined using known computer algorithms such as the "FASTA" program, for example, using default parameters as in Pearson et al (1988) [Proc. Natl. Acad. Sci. USA 85]: 2444. Alternatively, it may be determined using Needleman-Wunsch algorithm (Needleman and Wunsch, 1970, J. Mol. Biol. 48:443-453) as performed in the Needleman program of the EMBOSS package (EMBOSS: The European Molecular Biology Open Software Suite, Rice et al., 2000, Trends Genet. 16:276-277) (version 5.0.0 or later) (including GCG program package ((Devereux, J., et al, Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.] (1988) SIAM J Applied Math 48:1073). For example, BLAST of the National Center for Biotechnology Information or ClustalW may be used to determine the homology, similarity, or identity.

The homology, similarity, or identity between polynucleotides or polypeptides may be determined by comparing sequence information using the GAP computer program as introduced by, for example, Needleman et al. (1970), J Mol Biol. 48:443, as disclosed by Smith and Waterman, Adv. Appl. Math (1981) 2:482. Briefly, the GAP program defines the homology, similarity, or identity as the value obtained by dividing the number of similarly aligned symbols (i.e., nucleotides or amino acids) by the total number of the symbols in the shorter of the two sequences. The default parameters for the GAP program may include: (1) a binary comparison matrix (containing a value 1 for identity and a value 0 for non-identity) and the weighted comparison matrix of Gribskov et al (1986) Nucl. Acids Res. 14:6745 as disclosed in Schwartz and Dayhoff, eds., Atlas Of Protein Sequence And Structure, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or a gap open penalty of 10 and a gap extension penalty of 0.5); and (3) no penalty for end gaps.

As used herein, the term "corresponding to" refers to an amino acid residue at a position listed in a polypeptide, or an amino acid residue similar to, identical to, or homologous to a residue listed in a polypeptide. Identifying the amino acid at the corresponding position may be determining a specific amino acid in a sequence that refers to a specific sequence. As used herein, the "corresponding region" generally refers to a similar or corresponding position in a related protein or a reference protein.

For example, an arbitrary amino acid sequence is aligned with SEQ ID NO: 1, and based on this, each amino acid residue of the amino acid sequence may be numbered with reference to the numerical position of the amino acid residue corresponding to the amino acid residue of SEQ ID NO: 1. For example, a sequence alignment algorithm as described in the present disclosure may determine the position of an amino acid, or a position at which modification such as substitution, insertion, or deletion occurs through comparison with that in a query sequence (also referred to as a "reference sequence").

For such alignments, for example, the Needleman-Wunsch algorithm (Needleman and Wunsch, 1970, J. Mol. Biol. 48:443-453), the Needleman program of the EMBOSS package (EMBOSS: The European Molecular Biology Open Software Suite, Rice et al., 2000), Trends Genet. 16:276-277), etc. may be used, but are not limited thereto, and a sequence alignment program, a pairwise sequence comparison algorithm, etc., which known in the art, may be appropriately used.

As used herein, the term "O-acetyl homoserine", which is a specific intermediate material in a methionine biosynthesis pathway of a microorganism, refers to an acetyl-derivative of L-homoserine. The O-acetyl homoserine may be produced by an enzyme activity of transferring an acetyl group of acetyl-CoA to homoserine using homoserine and acetyl-CoA as substrates.

As used herein, the term "microorganism (or strain)" includes all of wild-type microorganisms or naturally or artificially genetically modified microorganisms, and it may be a microorganism in which a specific mechanism is weakened or strengthened due to insertion of a foreign gene or an activity enhancement or inactivation of an endogenous gene, and it may be a microorganism including genetic modification for production of a desired polypeptide, protein, or product.

As used herein, the term "microorganism with O-acetyl homoserine-producing ability" includes a microorganism, which, being a eukaryotic or prokaryotic microorganism capable of producing O-acetyl homoserine within a living organism, is provided with O-acetyl homoserine-producing ability to its parent microorganism without O-acetyl homoserine-producing ability, or a microorganism which is endogenously provided with the O-acetyl homoserine-producing ability. O-Acetyl homoserine-producing ability may be provided or promoted by improvement of species. The microorganism with O-acetyl homoserine-producing ability may be a strain producing L-lysine, L-threonine, L-isoleucine, or L-methionine, or may be derived therefrom, but is not limited thereto.

With respect to the objects of the present disclosure, the microorganism producing O-acetyl homoserine is characterized in that the desired O-acetyl homoserine-producing ability is enhanced by weakening the activity of GNAT family N-acetyltransferase protein, as compared to endogenous activity, and may be a genetically modified microorganism or a recombinant microorganism, but is not limited thereto. Specifically, the recombinant strain with the increased O-acetyl homoserine-producing ability may be a microorganism in which the O-acetyl homoserine-producing ability is increased, as compared to the natural wild-type microorganism or an unmodified microorganism with the endogenous activity of the GNAT family N-acetyltransferase protein, but is not limited thereto.

For example, the microorganism producing O-acetyl homoserine may be a microorganism endogenously including the protein consisting of the amino acid sequence of SEQ ID NO: 1, or a protein consisting of an amino acid sequence having at least 70%, 75%, 80%, 85%, 90%, 95%, 96%, 97%, 98%, 99%, 99.5%, 99.7%, or 99.9% or more homology or identity to SEQ ID NO: 1.

For example, the microorganism producing O-acetyl homoserine may be a microorganism endogenously including a polynucleotide sequence encoding a protein including an amino acid sequence having at least 80% homology to SEQ ID NO: 1, or a nucleotide sequence of SEQ ID NO: 2, or a nucleotide sequence having 70% or more, 75% or more, 80% or more, 85% or more, 90% or more, 95% or more, 96% or more, 97% or more, 98% or more, and less than 100% homology or identity to the sequence of SEQ ID NO: 2.

For example, the microorganism having the increased production ability may have an increased O-acetyl homoserine-producing ability of about 1% or more, specifically, about 1% or more, about 5% or more, about 10% or more, about 15% or more, about 20% or more, about 21% or more, about 22% or more, about 23% or more, about 24% or more, about 25% or more, about 26% or more, about 27% or more, about 28% or more, about 29% or more, or about 30% or more (the upper limit is not particularly limited, but may be, for example, about 100% or less, about 50% or less, about 45% or less, or about 40% or less, or about 35% or less), as compared to that of the parent strain before modification or the unmodified microorganism having the endogenous activity of the GNAT family N-acetyltransferase protein, but the increased amount is not limited thereto as long as the production ability has an increased amount of a +value, as compared to the production ability of the parent strain before modification or the unmodified microorganism. In another example, the recombinant strain having the increased production ability may have an increased O-acetyl homoserine-producing ability of about 1.1 times or more, about 1.2 times or more, about 1.21 times or more, about 1.22 times or more, about 1.23 times or more, about 1.24 times or more, about 1.25 times or more, about 1.26 times or more, about 1.27 times or more, about 1.28 times or more, about 1.29 times or more, about 1.30 times or more (the upper limit is not particularly limited, but may be, for example, about 10 times or less, about 5 times or less, about 3 times or less, about 2 times or less, about 1.5 times or less, or about 1.4 times or less), as compared to that of the parent strain before modification or the unmodified microorganism, but is not limited thereto.

As used herein, the term "unmodified microorganism" does not exclude strains including mutation that may occur naturally in microorganisms, and may be a wild-type strain or a natural strain itself or may be a strain before the trait is changed by genetic variation due to natural or artificial factors. For example, the unmodified microorganism may refer to a strain in which the GNAT family N-acetyltransferase protein activity described herein is not weakened or has not yet been weakened, as compared to the endogenous activity. The "unmodified microorganism" may be used interchangeably with "strain before being modified", "microorganism before being modified", "unvaried strain", "unmodified strain", "unvaried microorganism", or "reference microorganism".

The microorganism having O-acetyl homoserine-producing ability may be either a prokaryotic cell or a eukaryotic cell, specifically, a prokaryotic cell. The prokaryotic cell may include, for example, microbial strains of the *Escherichia* sp., *Erwinia* sp., *Serratia* sp., *Providencia* sp., *Corynebacterium* sp., *Pseudomonas* sp., *Leptospira, Salmonella* sp., *Brevibacteria* sp., *Hypomononas* sp., *Chromobacterium* sp. and *Norcardia* sp., or fungi, or yeasts. Specifically, the prokaryotic cell may be a microbial strain of the *Escherichia* sp., *Corynebacterium* sp., *Leptospira* sp., or a fungus. More specifically, it may be a microbial strain of the *Corynebacterium* sp.

In the present disclosure, the "microorganism of the *Corynebacterium* sp." may include all microorganisms of the *Corynebacterium* sp. Specifically, it may be *Corynebacterium glutamicum, Corynebacterium crudilactis, Corynebacterium deserti, Corynebacterium efficiens, Corynebacterium callunae, Corynebacterium stationis, Corynebacterium singulare, Corynebacterium halotolerans, Corynebacterium striatum, Corynebacterium ammoniagenes, Corynebacterium pollutisoli, Corynebacterium imitans, Corynebacterium testudinoris*, or *Corynebacterium flavescens*, more specifically, *Corynebacterium glutamicum.*

The unmodified microorganism may be a microorganism including an amino acid sequence consisting of SEQ ID NO: 1 or a polynucleotide consisting of SEQ ID NO: 2.

Meanwhile, it was already known that the microorganism of the *Corynebacterium* sp. is able to produce O-acetyl homoserine, but its production ability is significantly low, and the genes or mechanisms responsible for the production mechanism have not been revealed. Accordingly, the microorganism of the *Corynebacterium* sp. producing O-acetyl homoserine of the present disclosure may include all of a natural wild-type microorganism itself, a microorganism of the *Corynebacterium* sp. with the improved O-acetyl homoserine-producing ability by strengthening or weakening the activity of genes related to the O-acetyl homoserine production mechanism, and a microorganism of the *Corynebacterium* sp. with the improved O-acetyl homoserine-producing ability by introducing or strengthening activity of a foreign gene.

As used herein, the term "weakening" of the activity of the polypeptide has a concept encompassing all of the weakening of activity or the absence of activity, as compared to the endogenous activity. The weakening may be used interchangeably with terms such as inactivation, deficiency, down-regulation, decrease, reduction, attenuation, etc.

Specifically, the weakening may be, but is not limited to, inactivating. The inactivating may mean that the protein is not expressed at all, as compared to a parent strain or a strain in which the protein consisting of the amino acid sequence of SEQ ID NO: 1 is not modified, or even through expressed, its activity is absent or weakened.

The weakening may also include a case where the activity of the polypeptide itself is weakened or eliminated due to variation of the polynucleotide encoding the polypeptide, etc., as compared to the activity of the polypeptide originally possessed by the microorganism, a case where the overall polypeptide activity level and/or concentration (expression level) in the cell is low due to inhibition of the expression of the gene of the polynucleotide encoding the polypeptide or due to inhibition of translation into the polypeptide, as compared to that of the natural strain, a case where the polynucleotide is not expressed at all, and/or a case where the polypeptide activity is absent even when the polynucleotide is expressed.

The "endogenous activity" means the activity of a specific polypeptide originally possessed by a parent strain before the trait is changed or a wild-type or unmodified microorganism, when the trait is changed by genetic variation due to natural or artificial factors. This may be used interchangeably with "activity before modification". The "inactivation, deficiency, decrease, down-regulation, reduction, or attenuation" of the activity of a polypeptide compared to the endogenous activity thereof means that the activity of the polypeptide is lowered, compared to the activity of a specific polypeptide originally possessed by a parent strain before the trait is changed or an unmodified microorganism.

Such weakening of the activity of the polypeptide may be performed by any method known in the art, but is not limited thereto, and may be achieved by applying various methods well known in the art (e.g., Nakashima N et al., Bacterial cellular engineering by genome editing and gene silencing. Int J Mol Sci. 2014; 15 (2): 2773-2793, Sambrook et al. Molecular Cloning 2012, etc.).

Specifically, the weakening of the activity of the polypeptide of the present disclosure may be achieved by:

1) deletion of the entirety or a part of the gene encoding the polypeptide;
2) modification of an expression control region (or expression control sequence) to reduce the expression of a gene encoding the polypeptide;
3) modification of the amino acid sequence constituting the polypeptide to eliminate or weaken the activity of the polypeptide (e.g., deletion/substitution/addition of one or more amino acids in the amino acid sequence);
4) modification of the gene sequence encoding the polypeptide to eliminate or weaken the activity of the polypeptide (e.g., deletion/substitution/addition of one or more nucleotides in the nucleotide sequence of the polypeptide gene to encode the polypeptide which is modified to eliminate or weaken the activity of the polypeptide);
5) modification of a nucleotide sequence encoding an initiation codon or 5'-UTR region of the gene transcript encoding the polypeptide;
6) introduction of an antisense oligonucleotide (e.g., antisense RNA) complementarily binding to the gene transcript encoding the polypeptide;
7) addition of a sequence complementary to the Shine-Dalgarno sequence of the gene encoding the polypeptide to the upstream of the Shine-Dalgarno sequence in order to form a secondary structure that makes the attachment of ribosomes impossible;
8) addition of a promoter, which is to be reverse-transcribed, to the 3' end of the open reading frame (ORF) of the gene sequence encoding the polypeptide (reverse transcription engineering, RTE); or
9) combination of two or more selected from 1) to 8), but is not particularly limited thereto.

For example,

1) The deletion of a part or the entirety of the gene encoding the polypeptide may be elimination of the entirety of the polynucleotide encoding an endogenous target polypeptide in the chromosome, replacement with a polynucleotide having deletion of some nucleotides, or replacement with a marker gene.

Further, 2) the modification of an expression control region (or expression control sequence) may be the mutation on the expression control region (or expression control sequence) through deletion, insertion, non-conservative or conservative substitution, or a combination thereof, or the replacement with a sequence having weaker activity. The expression control region includes a promoter, an operator sequence, a sequence for encoding a ribosomal binding site, and a sequence for controlling the termination of transcription and translation, but is not limited thereto.

Further, 3) and 4) the modification of the amino acid sequence or the polynucleotide sequence may be the mutation on the sequence through deletion, insertion, non-conservative or conservative substitution, or a combination thereof in the amino acid sequence of the polypeptide or the polynucleotide sequence encoding the polypeptide, or a replacement with an amino acid sequence or polynucleotide sequence improved to have weaker activity, or an amino acid sequence or polynucleotide sequence improved to have no activity, so as to weaken activity of the polypeptide, but is not limited thereto. For example, the expression of the gene may be inhibited or attenuated by introducing mutation into the polynucleotide sequence to form a termination codon, but is not limited thereto.

Further, 5) the modification of a nucleotide sequence encoding an initiation codon or 5'-UTR region of the gene transcript encoding the polypeptide may be, for example, the substitution with a nucleotide sequence encoding, rather than an endogenous initiation codon, another initiation codon having a lower expression rate of the polypeptide, but is not limited thereto.

6) The introduction of an antisense oligonucleotide (e.g., antisense RNA) complementarily binding to the gene transcript encoding the polypeptide may be referred to, for example, a literature [Weintraub, H. et al., Antisense-RNA as a molecular tool for genetic analysis, Reviews—Trends in Genetics, Vol. 1(1) 1986].

7) The addition of a sequence complementary to the Shine-Dalgarno sequence of the gene encoding the polypeptide to the upstream of the Shine-Dalgarno sequence so as to form a secondary structure that makes the attachment of ribosomes impossible may be making mRNA translation impossible or reducing the rate thereof.

8) The addition of a promoter, which is to be reverse-transcribed, to the 3' end of the open reading frame (ORF) of the gene sequence encoding the polypeptide (reverse transcription engineering, RTE) may be making an antisense nucleotide complementary to the gene transcript encoding the polypeptide to weaken the activity.

Specifically, the microorganism having O-acetyl homoserine-producing ability of the present disclosure may be a microorganism in which the GNAT family N-acetyltransferase protein activity is inactivated, but is not limited thereto.

Specifically, to inactivate the GNAT family N-acetyltransferase protein activity, a method of deleting a part or the entirety of the gene encoding the protein may be used. Specifically, this may be performed by replacing the polynucleotide encoding the endogenous target protein in the chromosome with a polynucleotide or marker gene with deletion of some nucleotide sequences via a vector for chromosome insertion in the microorganism. As an example for the method of deleting a part or the entirety of the polynucleotide, a method of deleting the polynucleotide by homologous recombination may be used, but is not limited thereto. As another example, the method of deleting a part or the entirety of the gene may be performed by inducing a mutation with light such as ultraviolet rays, or chemicals, and then selecting, from the obtained mutants, a strain in which the target gene is deleted.

The gene deletion method includes a method of using a genetic recombination technique. For example, this may be achieved by injecting a polynucleotide sequence or vector containing a polynucleotide sequence homologous to the target gene into the microorganism to cause homologous recombination. Further, the polynucleotide sequence or vector to be injected may include a dominant selection marker, but is not limited thereto.

As used herein, the term “polynucleotide” is a DNA or RNA strand having a certain length or more as a polymer of nucleotides in which nucleotide monomers are connected in a long chain by covalent bonds, and more specifically, refers to a polynucleotide fragment encoding the variant.

In the present disclosure, the GNAT family N-acetyltransferase may be encoded by a gene including the polynucleotide sequence of SEQ ID NO: 2, but is not limited thereto. More specifically, the GNAT family N-acetyltransferase may be encoded by a gene having and/or including the polynucleotide sequence of SEQ ID NO: 2, or a gene essentially consisting of or consisting of the polynucleotide sequence, but is not limited thereto. The nucleotide sequence of SEQ ID NO: 2 may be obtained from known databases, and examples thereof may include the NCBI GenBank, etc., but are not limited thereto.

In the present disclosure, the gene including the nucleotide sequence of SEQ ID NO: 2 may be used interchangeably with a polynucleotide including the nucleotide sequence of SEQ ID NO: 2, a gene or polynucleotide having the nucleotide sequence of SEQ ID NO: 2, or a gene or polynucleotide consisting of the nucleotide sequence of SEQ ID NO: 2.

The polynucleotide of the present disclosure may undergo various modifications in the coding region within the scope that does not change the amino acid sequence of the variant of the present disclosure in consideration of codon degeneracy or codons preferred in organisms that are intended to express the variant of the present disclosure. Specifically, as the polynucleotide of the present disclosure, any polynucleotide sequence may be included in the scope of the present disclosure, as long as it is able to encode a protein including an amino acid sequence having at least 80% homology to SEQ ID NO: 1, and it may have or include the nucleotide sequence of SEQ ID NO: 2, or a nucleotide sequence having 70% or more, 75% or more, 80% or more, 85% or more, 90% or more, 95% or more, 96% or more, 97% or more, 98% or more, and less than 100% homology or identity to the sequence of SEQ ID NO: 2, or may consist of or essentially consist of the nucleotide sequence of SEQ ID NO: 2, or a nucleotide sequence having 70% or more, 75% or more, 80% or more, 85% or more, 90% or more, 95% or more, 96% or more, 97% or more, 98% or more, and less than 100% homology or identity to the sequence of SEQ ID NO: 2, but is not limited thereto.

Further, the polynucleotide of the present disclosure may include a probe that may be prepared from a known gene sequence, for example, may include any sequence without limitation as long as it is a sequence that is able to hybridize with a complementary sequence to the entirety or a part of the polynucleotide sequence of the present disclosure under stringent conditions. The “stringent conditions” mean conditions that enable specific hybridization between polynucleotides. These conditions are specifically described in documents (see J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York, 9.50-9.51, 11.7-11.8). Examples thereof include a condition in which polynucleotides having higher homology or identity, i.e., polynucleotides having 70% or more, 75% or more, 80% or more, 85% or more, 90% or more, 95% or more, 96% or more, 97% or more, 98% or more, or 99% or more homology or identity are hybridized with each other while polynucleotides having lower homology or identity are not hybridized with each other, or a condition in which washing is performed once, specifically, twice to three times at a salt concentration and temperature equivalent to 60° C., 1×SSC, 0.1% SDS, specifically 60° C., 0.1×SSC, 0.1% SDS, more specifically 68° C., 0.1×SSC, 0.1% SDS, which are washing conditions for common Southern hybridization.

Hybridization requires that two nucleic acids have complementary sequences, although mismatches between bases are allowed depending on the stringency of hybridization. The term "complementary" is used to describe the relation between nucleotide bases capable of being hybridized with each other. For example, with regard to DNA, adenine is complementary to thymine and cytosine is complementary to guanine. Hence, the polynucleotide of the present disclosure may also include substantially similar nucleic acid sequences as well as isolated nucleic acid fragments that are complementary to the entire sequence.

Specifically, a polynucleotide having homology or identity to the polynucleotide of the present disclosure may be detected using a hybridization condition including a hybridization step at a Tm value of 55° C. and the above-described conditions. Further, the Tm value may be 60° C., 63° C., or 65° C., but is not limited thereto, and may be appropriately adjusted by those skilled in the art according to the purpose.

The appropriate stringency to hybridize the polynucleotide depends on the length and degree of complementarity of the polynucleotide, and the variables are well known in the art (e.g., J. Sambrook et al., supra).

Specifically, the microorganism having O-acetyl homoserine-producing ability of the present disclosure may be a microorganism in which activity of the GNAT family N-acetyltransferase protein is inactivated, but is not limited thereto.

Specifically, the microorganism having O-acetyl homoserine-producing ability of the present disclosure may be a microorganism in which the polynucleotide encoding GNAT family N-acetyltransferase is deleted, but is not limited thereto. More specifically, the microorganism having O-acetyl homoserine-producing ability of the present disclosure may be a microorganism in which the nucleotide sequence of SEQ ID NO: 2 is deleted, but is not limited thereto.

With respect to the objects of the present disclosure, the microorganism includes an expression vector for inactivating the GNAT family N-acetyltransferase protein in a host cell, thereby inactivating activity of the GNAT family N-acetyltransferase protein, but is not limited thereto.

The vector of the present disclosure may include a DNA construct including a nucleotide sequence of a polynucleotide encoding a desired polypeptide which is operably linked to a suitable expression regulatory region (or expression control sequence) so that the desired polypeptide may be expressed in a suitable host. The expression regulatory region may include a promoter capable of initiating transcription, any operator sequence for controlling the transcription, a sequence encoding a suitable mRNA ribosome binding site, and a sequence controlling termination of transcription and translation. The vector may be transformed into a suitable host cell, and then replicated or function independently of the host genome, or may be integrated into the genome itself.

The vector used in the present disclosure is not particularly limited, but any vector known in the art may be used. Examples of commonly used vectors include natural or recombinant plasmids, cosmids, viruses, and bacteriophages. For example, pWE15, M13, MBL3, MBL4, IXII, ASHII, APII, t10, t11, Charon4A, Charon21A, etc. may be used as a phage vector or a cosmid vector, and pDZ system, pBR system, pUC system, pBluescript II system, pGEM system, pTZ system, pCL system, pSK system, pSKH system, pET system, etc. may be used as a plasmid vector. Specifically, pDZ, pDC, pDCM2, pACYC177, pACYC184, pCL, pSK, pSKH130, pECCG117, pUC19, pBR322, pMW118, pCC1BAC vector, etc. may be used.

For example, a polynucleotide encoding a desired polypeptide may be inserted into a chromosome through a vector for intracellular chromosome insertion. The Insertion of the polynucleotide into the chromosome may be performed by any method known in the art, for example, homologous recombination, but is not limited thereto. The vector may further include a selection marker for the confirmation of chromosome insertion. The selection marker is for selecting the cells transformed with vectors, i.e., for confirming the insertion of a desired nucleic acid molecule, and markers that confer selectable phenotypes such as drug resistance, auxotrophy, resistance to cytotoxic agents, or expression of surface polypeptides may be used. In an environment treated with a selective agent, only cells expressing the selection marker survive or exhibit other phenotypic traits, and thus transformed cells may be selected.

As used herein, the term "transformation" means that a vector including a polynucleotide encoding a target polypeptide is introduced into a host cell or a microorganism so that the polypeptide encoded by the polynucleotide may be expressed in the host cell. The transformed polynucleotide may be located regardless of the position, either by being inserted into the chromosome of the host cell or located outside the chromosome as long as it may be expressed in the host cell. Further, the polynucleotide includes DNA and/or RNA encoding a desired polypeptide. The polynucleotide may be introduced in any form as long as it may be introduced into a host cell and expressed. For example, the polynucleotide may be introduced into a host cell in the form of an expression cassette, which is a gene construct containing all elements required for self-expression. The expression cassette may usually include a promoter operably linked to the polynucleotide, a transcription termination signal, a ribosome binding site, and a translation termination signal. The expression cassette may be in the form of an expression vector capable of self-replicating. Further, the polynucleotide may be introduced into a host cell in its own form and operably linked to a sequence required for expression in the host cell, but is not limited thereto.

Further, the term "operably linked" means that the polynucleotide sequence is functionally linked to a promoter sequence that initiates and mediates transcription of the polynucleotide encoding the desired variant of the present disclosure.

The modification of a part or the entirety of the polynucleotide in the microorganism of the present disclosure may be induced by: (a) homologous recombination using a vector for chromosomal insertion in a microorganism or genome editing using engineered nuclease (e.g., CRISPR-Cas9), or and/or (b) the treatment with light, such as ultraviolet light and radiation, and/or chemicals, but is not limited thereto. The method of modifying a part or the entirety of the gene may include a method by DNA recombinant technology. For example, a nucleotide sequence or vector containing a nucleotide sequence homologous to a target gene may be introduced into the microorganism to bring about homologous recombination, resulting in deletion in a part or the entirety of the gene. The nucleotide sequence or vector to be introduced may include a dominant selection marker, but is not limited thereto.

As used herein, the term "enhancement" of the polypeptide activity means that the activity of the polypeptide is increased, as compared to the endogenous activity thereof. The enhancement may be used interchangeably with terms such as activation, up-regulation, overexpression, and increase, etc. Here, the activation, enhancement, up-regulation, overexpression, and increase may include both cases in which an activity not originally possessed is exhibited, or the activity is enhanced, as compared to the endogenous activity or the activity before modification. The "endogenous activity" means the activity of a specific polypeptide originally possessed by a parent strain before the trait is changed or an unmodified microorganism, when the trait is changed by genetic variation due to natural or artificial factors. This may be used interchangeably with "activity before modification". The fact that the activity of a polypeptide is "enhanced", "up-regulated", "overexpressed", or "increased, as compared to the endogenous activity means that the activity of the polypeptide is improved as compared to the activity and/or concentration (expression level) of the specific polypeptide originally possessed by a parent strain before the trait is changed or an unmodified microorganism.

The enhancement may be achieved through the introduction of a foreign polypeptide or the enhancement of the activity of the endogenous polypeptide, and/or concentration (expression level). The enhancement of the activity of the polypeptide may be confirmed by increase in the degree of activity and the expression level of the corresponding polypeptide or increase in the amount of the product released from the corresponding polypeptide.

For the enhancement of the activity of the polypeptide, various methods well known in the art may be applied, and the method is not limited as long as the activity of the desired polypeptide may be enhanced as compared to that of the microorganism before modification. Specifically, genetic engineering and/or protein engineering well known to those skilled in the art, which are routine methods of molecular biology, may be used, but the method is not limited thereto (e.g., Sitnicka et al. Functional Analysis of Genes. Advances in Cell Biology. 2010, Vol. 2. 1-16, Sambrook et al. Molecular Cloning 2012, etc.).

Specifically, the enhancement of the polypeptide of the present disclosure may be:

1) increase in the intracellular copy number of the polynucleotide encoding the polypeptide;
2) modification of a gene expression regulatory region on a chromosome encoding the polypeptide (e.g., occurrence of variations in the expression regulatory region, replacement with a sequence having stronger activity, or insertion of a sequence having stronger activity);
3) modification of a nucleotide sequence encoding an initiation codon or 5'-UTR region of the gene transcript encoding the polypeptide;
4) modification of the amino acid sequence of the polypeptide to enhance the activity of the polypeptide;
5) modification of the polynucleotide sequence encoding the polypeptide to enhance the activity of the polypeptide (e.g., modification of the polynucleotide sequence of the polypeptide gene to encode the polypeptide that has been modified to enhance the activity of the polypeptide);
6) introduction of a foreign polypeptide exhibiting the activity of the polypeptide or a foreign polynucleotide encoding the same;
7) codon optimization of the polynucleotide encoding the polypeptide;
8) analysis of the tertiary structure of the polypeptide to select and to modify or chemically modify the exposed site; or
9) a combination of two or more selected from 1) to 8), but is not particularly limited thereto.

More specifically, 1) the increase in the intracellular copy number of the polynucleotide encoding the polypeptide may be achieved by introducing, into a host cell, a vector which may replicate and function independently of the host and to which the polynucleotide encoding the corresponding polypeptide is operably linked. Alternatively, the increase may be achieved by introducing one copy or two or more copies of the polynucleotide encoding the corresponding polypeptide into a chromosome of a host cell. The introduction into the chromosome may be performed by introducing, into a host cell, a vector capable of inserting the polynucleotide into a chromosome of the host cell, but is not limited thereto. The vector is as described above.

2) The replacement of a gene expression regulatory region (or expression control sequence) on a chromosome encoding the polypeptide with a sequence exhibiting strong activity may be, for example, occurrence of variation in a sequence due to deletion, insertion, nonconservative or conservative substitution, or a combination thereof, or replacement with a sequence exhibiting stronger activity so that the activity of the expression regulatory region is further enhanced. The expression regulatory region may include, but is not particularly limited to, a promoter, an operator sequence, a sequence encoding a ribosome binding site, a sequence controlling the termination of transcription and translation, etc. For example, the replacement may be to replace the original promoter with a strong promoter, but is not limited thereto.

Examples of known strong promoters include CJ1 to CJ7 promoters (U.S. Pat. No. 7,662,943 B2), a lac promoter, a trp promoter, a trc promoter, a tac promoter, a lambda phage PR promoter, a PL promoter, a tet promoter, a gapA promoter, a SPL7 promoter, a SPL13 (sm3) promoter (U.S. Pat. No. 10,584,338 B2), an O2 promoter (U.S. Pat. No. 10,273,491 B2), a tkt promoter, an yccA promoter, etc., but is not limited thereto.

3) The modification of a nucleotide sequence encoding an initiation codon or 5'-UTR region of the gene transcript encoding the polypeptide may be, for example, substitution with another initiation codon having a higher polypeptide expression rate as compared to an endogenous initiation codon, but is not limited thereto.

4) and 5) The modification of the amino acid sequence or the polynucleotide sequence may be occurrence of variation in the sequence due to deletion, insertion, nonconservative or conservative substitution of the amino acid sequence of the polypeptide or the polynucleotide sequence encoding the polypeptide, or a combination thereof, or replacement with an amino acid sequence or polynucleotide sequence improved to exhibit stronger activity or an amino acid sequence or polynucleotide sequence improved to be more active so that the activity of the polypeptide is enhanced, but is not limited thereto. The replacement may be specifically performed by inserting a polynucleotide into a chromosome by homologous recombination, but is not limited thereto. The vector used here may further include a selection marker for the confirmation of chromosome insertion. The selection marker is as described above.

6) The introduction of a foreign polynucleotide exhibiting the activity of the polypeptide may be introduction of a foreign polynucleotide into a host cell, the foreign polynucleotide encoding a polypeptide exhibiting activity identical or similar to that of the polypeptide. There is no limitation on its origin or sequence as long as the foreign polynucleotide exhibits activity identical or similar to that of the polypeptide. The method used in the introduction may be performed by appropriately selecting a known transformation method by those skilled in the art. As the introduced polynucleotide is expressed in the host cell, the polypeptide may be produced and the activity thereof may be increased.

7) The codon optimization of the polynucleotide encoding the polypeptide may be codon optimization of an endogenous polynucleotide so as to enhance transcription or translation in a host cell, or codon optimization of a foreign polynucleotide so as to perform optimized transcription and translation in a host cell.

8) The analysis of the tertiary structure of the polypeptide to select and to modify or chemically modify the exposed site may be, for example, to determine a template protein candidate according to the degree of similarity of the sequence by comparing the sequence information of a polypeptide to be analyzed with a database storing the sequence information of known proteins, to confirm the structure based on this, and to modify or chemically modify the exposed site to be modified or chemically modified.

Such enhancement of the polypeptide activity may be an increase in the activity or concentration/expression level of the corresponding polypeptide, based on the activity or concentration of the polypeptide expressed in a wild-type or a microbial strain before being modified, or an increase in the amount of a product produced from the corresponding polypeptide, but is not limited thereto.

In the microorganism having O-acetyl homoserine-producing ability of the present disclosure, the activity of L-methionine/branched-chain amino acid exporter YjeH protein may be further enhanced, but is not limited thereto.

As used herein, the term "L-methionine/branched-chain amino acid exporter YjeH" is a member of the amino acid efflux (AAE) within the amino acid-polyamine-organocation (APC) family of transporters, and is a protein that mediates export of O-acetyl homoserine and/or homoserine outside cells. YjeH is predicted to contain 12 transmembrane α helices, 10 of which form an inverted repeat fold that is characteristic of the APC superfamily. Protein and gene sequences of the L-methionine/branched-chain amino acid exporter YjeH may be obtained from known databases, and examples thereof may include the NCBI GenBank, etc., but are not limited thereto. Further, it may be, for example, derived from *Escherichia coli* (*E. coli*), but is not limited thereto. In the present disclosure, the L-methionine/branched-chain amino acid exporter YjeH protein may be used interchangeably with an inner membrane protein, an O-acetyl homoserine exporter protein, a protein having O-acetyl homoserine-exporting ability, a protein having O-acetyl homoserine exporting activity, YjeH protein, or YjeH.

Specifically, the microorganism having O-acetyl homoserine-producing ability of the present disclosure may further include a variant of the L-methionine/branched-chain amino acid exporter YjeH, but is not limited thereto. More specifically, the microorganism having O-acetyl homoserine-producing ability of the present disclosure may have enhanced activity of the L-methionine/branched-chain amino acid exporter YjeH protein by further introducing the variant of the L-methionine/branched-chain amino acid exporter YjeH, but is not limited thereto.

More specifically, the variant of the L-methionine/branched-chain amino acid exporter YjeH may increase O-acetyl homoserine-producing ability by increasing the amount of O-acetyl homoserine exported by the microorganism, and may have and/or may include an amino acid sequence represented by SEQ ID NO: 10, or may essentially consist of or may consist of the amino acid sequence.

Further, the variant of the L-methionine/branched-chain amino acid exporter YjeH may include the amino acid sequence represented by SEQ ID NO: 10 as well as an amino acid sequence having at least 70%, 75%, 80%, 85%, 90%, 95%, 96%, 97%, 98%, 99%, 99.5%, 99.7%, or 99.9% or more homology or identity to SEQ ID NO: 10. It is also apparent that any having an amino acid sequence with deletion, modification, substitution, conservative substitution, or addition in part of the sequence may also be included within the scope of the present disclosure as long as the amino acid sequence has such homology or identity and has biological activity identical or corresponding to that of the variant of the L-methionine/branched-chain amino acid exporter YjeH of the present disclosure.

For example, the microorganism having O-acetyl homoserine-producing ability of the present disclosure may be a microorganism in which the O-acetyl homoserine-producing ability is further increased by further including, specifically, further introducing a protein consisting of the amino acid sequence of SEQ ID NO: 10, or a protein consisting of an amino acid sequence having at least 70%, 75%, 80%, 85%, 90%, 95%, 96%, 97%, 98%, 99%, 99.5%, 99.7%, or 99.9% or more homology or identity to SEQ ID NO: 10.

Specifically, "introduction of the protein" means exhibiting activity of a particular protein by expressing a gene in a microorganism, the gene that was not originally possessed by the microorganism, or exhibiting increased or enhanced activity, as compared with the endogenous activity of the corresponding protein or the activity before modification. For example, a polynucleotide encoding a particular protein may be introduced into a chromosome in a microorganism or a vector containing a polynucleotide encoding a particular protein may be introduced into a microorganism to exhibit its activity.

With respect to the objects of the present disclosure, the microorganism including the variant of L-methionine/branched-chain amino acid exporter YjeH may refer to a microorganism in which the O-acetyl homoserine-exporting ability is increased by introducing the variant of L-methionine/branched-chain amino acid exporter YjeH into a microorganism having a naturally weak O-acetyl homoserine-exporting ability. Specifically, the microorganism may be charactered in that the variant of L-methionine/branched-chain amino acid exporter YjeH is introduced to increase the extracellular release of O-acetyl homoserine, as compared to the wild-type or unmodified microorganism, thereby increasing the production of O-acetyl homoserine. This is because the release of O-acetyl homoserine from the microorganism is increased by introducing the variant of L-methionine/branched-chain amino acid exporter YjeH, thereby increasing production of O-acetyl homoserine, whereas the wild-type or unmodified microorganisms does not release O-acetyl homoserine, or produces a trace amount thereof even though it releases O-acetyl homoserine.

Examples of the transmembrane protein YjeH and/or variant thereof applied to the present disclosure are disclosed in Korean Patent No. 10-2182497, and the disclosure of the patent is incorporated herein by reference in its entirety.

In the microorganism having O-acetyl homoserine-producing ability of the present disclosure, the activity of homoserine acetyl transferase (MetX) may be further enhanced, but is not limited thereto.

As used herein, the term "MetX" refers to a homoserine acetyl transferase. Specifically, most microorganisms present in nature utilize O-succinyl homoserine or O-acetyl homoserine as intermediates for the biosynthesis of methionine. Generally, MetA produces O-succinyl homoserine, and homoserine O-acetyl transferase produces O-acetyl homoserine. Unlike MetA, MetX is not feedback inhibited and have high enzyme stability. Protein and gene sequences of the MetX may be obtained from known databases, and examples thereof may include the NCBI GenBank, etc., but are not limited thereto. As used herein, the term “homoserine acetyl transferase” may be used interchangeably with “MetX”, “homoserine O-acetyl transferase”.

Specifically, in the microorganism having O-acetyl homoserine-producing ability of the present disclosure, the expression of the metX gene encoding O-acetyl homoserine transferase may be further amplified, but is not limited thereto.

A nucleotide sequence of the metX gene may be obtained from a known database, NCBI GenBank. As the polynucleotide encoding MetX, any polynucleotide sequence may be included in the scope of the present disclosure, as long as it is a polynucleotide sequence capable of encoding a protein including an amino acid sequence having at least 80% homology to the MetX, and may have or may include a nucleotide sequence of SEQ ID NO: 26 or a nucleotide sequence having 70% or more, 75% or more, 80% or more, 85% or more, 90% or more, 95% or more, 96% or more, 97% or more, 98% or more, and less than 100% homology or identity to the sequence of SEQ ID NO: 26, or may consist of or may essentially consist of the nucleotide sequence of SEQ ID NO: 26 or a nucleotide sequence having 70% or more, 75% or more, 80% or more, 85% or more, 90% or more, 95% or more, 96% or more, 97% or more, 98% or more, and less than 100% homology or identity to the sequence of SEQ ID NO: 26, but is not limited thereto.

Examples of the metX gene applied to the present disclosure are disclosed in Korean Patent No. 10-2182497, and the disclosure of the patent is incorporated herein by reference in its entirety.

In the microorganism having O-acetyl homoserine-producing ability of the present disclosure, the activity of aspartokinase may be further enhanced, but is not limited thereto.

Specifically, in order to increase the biosynthesis of O-acetyl-homoserine, the aspartokinase activity may be further enhanced, as compared to the unmodified microorganism, and particularly, a mutation (L377K) (Korean Patent Publication No. 10-2019-0003019) for releasing feedback inhibition of L-lysine and L-threonine of the gene (lysC) encoding aspartokinase may be introduced, but is not limited thereto. A nucleotide sequence of the lysC may be obtained from known databases, and any nucleotide sequence encoding the protein having the aspartokinase activity may be included without limitation, and example thereof may have a nucleotide sequence of SEQ ID NO: 21.

In the microorganism having O-acetyl homoserine-producing ability of the present disclosure, the activity of cystathionine gamma synthase may be further weakened, but is not limited thereto.

Specifically, the weakening may be inactivating, but is not limited thereto.

Specifically, the activity of cystathionine gamma synthase may be reduced or inactivated, as compared to that of an unmodified microorganism, and particularly, a gene (metB) encoding cystathionine synthase may be deleted, but is not limited thereto. As used herein, the term “cystathionine gamma synthase” may be used interchangeably with “cystathionine synthase”. A nucleotide sequence of the metB may be obtained from known databases, and any nucleotide sequence encoding the protein having the cystathionine synthase activity may be included without limitation, and example thereof may have a nucleotide sequence of SEQ ID NO: 11.

In the microorganism having O-acetyl homoserine-producing ability of the present disclosure, the activity of O-acetylhomoserine (thiol)-lyase may be further weakened, but is not limited thereto.

Specifically, the weakening may be inactivating, but is not limited thereto.

Specifically, the activity of O-acetyl homoserine thiol-lyase may be reduced or inactivated, as compared to that of an unmodified microorganism, and particularly, a gene (metY) encoding O-acetyl homoserine thiol-lyase may be deleted, but is not limited thereto. A nucleotide sequence of the metY may be obtained from known databases, and any nucleotide sequence encoding the protein having the O-acetyl homoserine thiol-lyase activity may be included without limitation, and example thereof may have a nucleotide sequence of SEQ ID NO: 16.

Another aspect of the present disclosure provides a method for producing O-acetyl homoserine, the method including the step of culturing the microorganism in a medium.

The microorganism and O-acetyl homoserine are as described above.

In the method of the present disclosure, the culturing of the microorganism may employ any culture conditions and culture methods known in the art. This culture procedure may be easily adjusted and used by those skilled in the art according to the selected strain.

As used herein, the term “culturing” refers to growing the microorganism of the present disclosure in appropriately adjusted environment conditions. The culture procedure of the present disclosure may be performed according to appropriate media or culture conditions known in the art. Such culturing process may be easily adjusted and used by a person skilled in the art according to the selected strain. Specifically, the culturing may be in a batch type, a continuous type, and a fed-batch type, but is not limited thereto.

As used herein, the “medium” refers to a mixture containing, as main ingredients, nutrient materials required for culturing the microorganism of the present disclosure, wherein the medium supplies nutrient materials including water essential for survival and growth, growth factors, etc. Specifically, as for the media and other culture conditions used for culturing the microorganism of the present disclosure, any medium that is commonly used for culturing microorganisms may be used without particular limitation. However, the microorganism of the present disclosure may be cultured under aerobic conditions in a common medium containing appropriate carbon sources, nitrogen sources, phosphorus sources, inorganic compounds, amino acids, and/or vitamins, while controlling the temperature, pH, etc.

In the present disclosure, the carbon source may include carbohydrates, such as glucose, saccharose, lactose, fructose, sucrose, maltose, etc.; sugar alcohols, such as mannitol, sorbitol, etc.; organic acids, such as pyruvic acid, lactic acid, citric acid, etc.; amino acids, such as glutamic acid, methionine, lysine, etc. In addition, natural organic nutrient sources may be used, such as starch hydrolysates, molasses, blackstrap molasses, rice bran, cassava, bagasse, and corn steep liquor, and specifically, carbohydrates, such as glucose and sterile pretreated molasses (i.e., molasses converted to reduced sugars) may be used, and appropriate amounts of various other carbon sources may be used without limitation. These carbon sources may be used alone or in a combination of two or more thereof, but are not limited thereto.

As for the nitrogen sources, inorganic nitrogen sources, such as ammonia, ammonium sulfate, ammonium chloride, ammonium acetate, ammonium phosphate, ammonium carbonate, ammonium nitrate, etc.; amino acids, such as glutamic acid, methionine, glutamine, etc.; and organic nitrogen sources, such as peptone, NZ-amine, meat extracts, yeast extracts, malt extracts, corn steep liquor, casein hydrolysates, fishes or decomposition products thereof, defatted soybean cake or degradation products thereof, etc. may be used. These nitrogen sources may be used alone or in a combination of two or more thereof, but are not limited thereto.

The phosphate sources may include potassium phosphate monobasic, potassium phosphate dibasic, and sodium-containing salts corresponding thereto. As for inorganic compounds, sodium chloride, calcium chloride, iron chloride, magnesium sulfate, iron sulfate, manganese sulfate, calcium carbonate, etc. may be used, and in addition, amino acids, vitamins, and/or suitable precursors may be included. These constituent ingredients or precursors may be added to the medium in a batch or continuous manner, but are not limited thereto.

The pH of the medium may be adjusted by adding compounds, such as ammonium hydroxide, potassium hydroxide, ammonia, phosphoric acid, and sulfuric acid, to the medium in an appropriate manner during culturing of the microorganism of the present disclosure. In addition, an anti-foaming agent, such as a fatty acid polyglycol ester, may be added to suppress foam formation during culturing. In addition, oxygen or oxygen-containing gas may be injected into the medium to maintain the aerobic state of the medium, or no gas may be injected or nitrogen, hydrogen or carbon dioxide gas may be injected to maintain the anaerobic or non-aerobic state of the medium, but is not limited thereto.

The culture temperature may be 25° C. to 40° C., more specifically 28° C. to 37° C., but is not limited thereto. The culturing may be continued until the desired production amount of the useful substance is obtained, and specifically for 1 hour to 100 hours, but is not limited thereto.

The O-acetyl homoserine produced by culturing of the present disclosure may be released into the medium or may remain in cells.

The method for producing O-acetyl homoserine of the present disclosure may further include the steps of preparing the microorganism of the present disclosure, preparing a medium for culturing the microorganism, or a combination thereof (regardless of the order, in any order), for example, before or after the culturing step.

The method for producing O-acetyl homoserine of the present disclosure may further include the step of recovering the O-acetyl homoserine from a medium resulting from the culturing (a medium in which culturing has been performed) or from the microorganism. The recovering step may be further included after the culturing step.

The recovering may be collecting the desired O-acetyl homoserine by using an appropriate method known in the art according to the method of culturing the microorganism of the present disclosure, for example, a batch, continuous, or fed-batch type culture. For example, centrifugation, filtration, treatment with a crystallized protein precipitating agent (salting-out), extraction, sonication, ultrafiltration, dialysis, various types of chromatography, such as molecular sieve chromatography (gel filtration), adsorption chromatography, ion exchange chromatography, and affinity chromatography, etc., HPLC, and a combination of these methods may be used, and the desired O-acetyl homoserine may be recovered from the medium or microorganism by using an appropriate method known in the art.

In addition, the method for producing O-acetyl homoserine of the present disclosure may further include a purification step. The purification may be performed by using an appropriate method known in the art. In an exemplary embodiment, when the method for producing O-acetyl homoserine of the present disclosure includes both the recovering step and the purification step, the recovering step and the purification step may be performed continuously or discontinuously regardless of the order, or may be performed simultaneously or integrated into one step, but is not limited thereto.

From the O-acetyl homoserine thus recovered, methionine may be produced by a two-step process (Korean Patent No. 10-0905381).

Still another aspect of the present disclosure provides a method for producing L-methionine, the method including the steps of culturing the microorganism in a medium, producing O-acetyl homoserine from the cultured microorganism or the medium, and converting the O-acetyl homoserine into L-methionine.

The microorganism, O-acetyl homoserine, and L-methionine are as described above.

The two-step process includes a process of producing L-methionine and organic acids using O-acetyl homoserine produced by the L-methionine precursor-producing strain and methyl mercaptan as substrates through an enzymatic reaction using an enzyme having O-acetyl homoserine sulfhydrylase activity or a strain including the enzyme.

More specifically, the present disclosure provides a method for producing L-methionine using the O-acetyl homoserine accumulated by the method as a substrate and using an enzymatic reaction of O-acetyl homoserine sulfhydrylase, etc.

In the two-step process, when O-acetyl homoserine is used as the L-methionine precursor, O-acetyl homoserine sulfhydrylase derived from a microbial strain of the *Leptospira* sp., *Chromobacterium* sp., or *Hyphomonas* sp, more specifically, *Leptospirameyeri, Pseudomonasaurogenosa, Hyphomonas Neptunium*, or *Chromobacterium Violaceum* may be used.

The reaction is as follows:

$CH_3SH$+O-acetyl homoserine<=>acetate+methionine

Such an additional methionine production process is disclosed in Korean Patent No. 10-0905381, and the disclosure of the patent is incorporated herein by reference in its entirety.

Still another aspect of the present disclosure provides a composition for producing O-acetyl homoserine, the composition including the microorganism.

The microorganism and O-acetyl homoserine are as described above.

The composition of the present disclosure may further include any appropriate excipient that is usually used in the composition for producing O-acetyl homoserine, and examples of the excipient may include a preserving agent, a wetting agent, a dispersing agent, a suspending agent, a buffer, a stabilizing agent, an isotonic agent, etc., but are not limited thereto.

Still another aspect of the present disclosure provides use of the microorganism for producing O-acetyl homoserine or L-methionine.

MODE FOR CARRYING OUT THE INVENTION

Hereinafter, the present disclosure will be described in more detail by way of exemplary embodiments. However, the following exemplary embodiments are only preferred embodiments for illustrating the present disclosure, and thus are not intended to limit the scope of the present disclosure thereto. Meanwhile, technical matters not described in the present specification may be sufficiently understood and easily implemented by those skilled in the technical field of the present disclosure or similar technical fields.

Example 1. Preparation of Endogenous Gene (NCgl0959)-Deleted Strain and Evaluation of O-Acetyl Homoserine and Homoserine-Producing Ability

Example 1-1. Preparation of Deletion Vector for NCgl0959 Deletion

To determine the effectiveness of an endogenous gene NCgl0959 in *Corynebacterium glutamicum* ATCC13032, a deletion vector was constructed, in which the gene NCgl0959 (SEQ ID NO: 2) was deleted.

In detail, to construct the NCgl0959 deletion vector, a pair of primers (SEQ ID NOS: 3 and 4) to amplify the 5' upstream region and a pair of primers (SEQ ID NOS: 5 and 6) to amplify the 3' downstream region, centering around the NCgl0959 gene of SEQ ID NO: 2, were designed. Primer sequences are as in Table 1 below.

TABLE 1

| SEQ ID NO. | Sequence name | Sequence |
|---|---|---|
| SEQ ID NO: 3 | 0959 _del up F | TGAATTCGAGCTCGGTACCCATCCACAGACGGTCATCGTG |
| SEQ ID NO: 4 | 0959_del up R | TTTGGTGgatatcCATGCACGCAATTGTCCTGG |
| SEQ ID NO: 5 | 0959_del down F | GTGCATGgatatcCACCAAATGGCAAGGATGCC |
| SEQ ID NO: 6 | 0959_del down R | GTCGACTCTAGAGGATCCCCGCAGAGATCGTTGATTCAAT |

PCR was performed using the chromosome of ATCC13032 wild-type (WT) as a template and primers of SEQ ID NO: 3 and SEQ ID NO: 4, and SEQ ID NO: 5 and SEQ ID NO: 6. PCR conditions were denaturation at 95° C. for 5 minutes, and then 30 cycles of denaturation at 95° C. for 30 seconds, annealing at 55° C. for 30 seconds, and polymerization at 72° C. for 30 seconds, followed by polymerization at 72° C. for 7 minutes. As a result, 1476 bp of a DNA fragment of the 5' upstream region and 1456 bp of a DNA fragment of the 3' downstream region, centering around the deletion site of the NCgl0959 gene, were obtained.

PCR was performed using the two amplified DNA fragments as templates and primers of SEQ ID NO: 3 and SEQ ID NO: 6. PCR conditions were denaturation at 95° C. for 5 minutes, and then 30 cycles of denaturation at 95° C. for 30 seconds, annealing at 55° C. for 30 seconds, and polymerization at 72° C. for 90 seconds, followed by polymerization at 72° C. for 7 minutes. As a result, 2912 bp of a DNA fragment containing the deletion site of the NCgl0959 gene was amplified.

A pDCM2 vector (SEQ ID NO: 7, Korean Patent Publication No. 10-2020-0136813) was treated with SmaI, and the PCR product (2912 bp of DNA fragment) obtained above and the pDCM2 vector treated with SmaI restriction enzyme were subjected to fusion cloning using an Infusion HD cloning kit (In-Fusion® HD Cloning Kit, Clontech). The cloned vector was transformed into *E. coli* DH5α, and the transformed *E. coli* was plated on an LB solid medium containing 25 mg/l of kanamycin. After selecting the colonies transformed with the plasmid from the LB solid medium, the plasmid was obtained using a plasmid extraction method (U.S. Pat. No. 5,981,235 A), and finally, a pDCM2-ΔNCgl0959 recombinant vector in which the NCgl0959 deletion cassette was cloned was constructed.

The constructed pDCM2-ΔNCgl0959 was transformed into the ATCC13032 strain using an electric pulse method, and through a secondary crossover process, ATCC13032 ΔNCgl0959 was obtained, in which the NCgl0959 gene was deleted on the chromosome. The inactivation of the NCgl0959 gene was finally confirmed by PCR using primers of SEQ ID NOS: 8 and 9, and then by comparing with ATCC13032, in which the NCgl0959 gene was not inactivated.

TABLE 2

| SEQ ID NO. | Sequence name | Sequence |
|---|---|---|
| SEQ ID NO: 8 | 0959_del F | GTGAAAAAACACTGGCAAAACAAGC |
| SEQ ID NO: 9 | 0959_del R | ATAAGAGGCACTCCCACAGATCACA |

Example 1-2. Evaluation of O-Acetyl Homoserine-Producing Ability in Wild-Type Strain To compare the O-acetyl homoserine (O-AH)-producing ability between ATCC13032 ΔNCgl0959 prepared in Example 1-1 and the wild-type strain ATCC13032, O-acetyl homoserine in culture media was analyzed by culturing in the following manner.

One platinum loop of the strain was inoculated into a 250 ml corner-baffled flask containing 25 ml of the following medium, and cultured at 33° C. for 20 hours with shaking at 200 rpm. The concentration of O-acetyl homoserine was analyzed using HPLC, and the analyzed concentration was as in Table 3.

<O-Acetyl Homoserine Production Medium (pH 7.2)>

30 g of glucose, 2 g of $KH_2PO_4$, 3 g of urea, 40 g of $(NH_4)_2SO_4$, 2.5 g of peptone, 5 g (10 ml) of CSL (Sigma), 0.5 g of $MgSO_4 \cdot 7H_2O$, 20 g of $CaCO_3$ (based on 1 liter of distilled water)

TABLE 3

(Results of flask)

| Strains | O—AH (g/L) |
|---|---|
| ATCC13032 | 0.27 |
| ATCC13032 Δ NCgl0959 | 0.30 |

As a result, as shown in Table 3 above, when ATCC13032 was cultured, 0.27 g/L of O-acetyl homoserine was accumulated, and ATCC13032 ΔNCgl0959, in which the endogenous gene NCgl0959 was deleted, accumulated 0.30 g/L of O-acetyl homoserine, indicating 120% production ability, relative to that of the control ATCC13032.

Example 2. Preparation of NCgl0959-Deleted Strain in Strain with Increased O-Acetyl Homoserine-Producing Ability and Evaluation of O-Acetyl Homoserine and Homoserine-Producing Ability-1

Example 2-1. Preparation of Strain

The pDCM2-ΔNCgl0959 vector constructed in Example 1-1 was transformed into KCCM12634P strain (KR 10-2182497, ATCC13032 ΔNCgl2335::PCJ7-yjeH (eco, F351L)) with increased O-acetyl homoserine-producing ability by an electric pulse method, and through a secondary crossover process, KCCM12634P ΔNCgl0959 was obtained, in which the NCgl0959 gene was deleted on the chromosome. The inactivation of the NCgl0959 gene was finally confirmed by PCR using primers of SEQ ID NOS: 8 and 9, and then by comparing with ATCC13032, in which the NCgl0959 gene was not inactivated.

Example 2-2. Evaluation of O-Acetyl Homoserine-Producing Ability

To compare the O-acetyl homoserine (O-AH)-producing ability between the KCCM12634P strain prepared in Example 2-1 and the KCCM12634P ΔNCgl0959 strain, O-acetyl homoserine in culture media was analyzed by culturing in the following manner.

One platinum loop of the strain was inoculated into a 250 ml corner-baffled flask containing 25 ml of the following medium, and cultured at 33° C. for 20 hours with shaking at 200 rpm. The concentration of O-acetyl homoserine was analyzed using HPLC, and the analyzed concentration was as in Table 4.

<O-Acetyl Homoserine Production Medium (pH 7.2)>

30 g of glucose, 2 g of $KH_2PO_4$, 3 g of urea, 40 g of $(NH_4)_2SO_4$, 2.5 g of peptone, 5 g (10 ml) of CSL (Sigma), 0.5 g of $MgSO_4·7H_2O$, 20 g of $CaCO_3$ (based on 1 liter of distilled water)

TABLE 4

(Results of flask)

| Strains | O—AH (g/L) |
|---|---|
| KCCM12634P | 1.05 |
| KCCM12634P Δ NCgl0959 | 1.31 |

As a result, as shown in Table 4 above, when NCgl0959 was deleted in the KCCM12634P strain, O-acetyl homoserine was 1.31 g/L, indicating about 130% production ability, relative to that of KCCM12634P. Therefore, the above results confirmed that the effect of increasing O-acetyl homoserine-producing ability due to NCgl0959 deletion was greater in the strain with the increased O-acetyl homoserine-producing ability.

Accordingly, the results of Examples 1-2 and 2-2 confirmed that deletion and inactivation of the NCgl0959 gene, which is the endogenous gene of ATCC13032 of the present disclosure, may improve the production ability of the desired amino acid.

Example 3. Preparation of NCgl0959-Deleted Strain in Strain with Increased O-Acetyl Homoserine-Producing Ability and Evaluation of O-Acetyl Homoserine and Homoserine-Producing Ability-2

Example 3-1. Preparation of Strain-1

Through PCR using chromosomal DNA of *Corynebacterium glutamicum* ATCC13032 as a template, the metB gene encoding cystathionine gamma-synthase in the O-acetyl homoserine degradation pathway was obtained. The nucleotide sequence information (NCBI No. Ncgl2360, SEQ ID NO: 11) of the metB gene was obtained from National Institutes of Health (NIH) GenBank, and based on this, primers (SEQ ID NOS: 12 and 13) containing a N-terminal region and a linker region of the metB gene and primers (SEQ ID NOS: 14 and 15) containing a C-terminal region and a linker region were synthesized. Primer sequences are listed in Table 5 below.

TABLE 5

| SEQ ID NO. | Sequence name | Sequence |
|---|---|---|
| SEQ ID NO: 12 | metB_N_del F | GGCTTCGGAGTTGGAGCG |
| SEQ ID NO: 13 | metB_N_del R | GCCAAATAGTTTcccgggGGTAGATCAACTCCTGTAATCA |
| SEQ ID NO: 14 | metB_C_del F | CAGGAGTTGATCTACCcccgggAAACTATTTGGCGGCAAG |
| SEQ ID NO: 15 | metB_C_del R | TCGCGTCTGGGTGCGCATC |

PCR was performed using the chromosomal DNA of ATCC13032 as a template and primers of SEQ ID NOS: 12 and 13 and SEQ ID NOS: 14 and 15. As a polymerase, PfuUltra™ high-fidelity DNA polymerase (Stratagene) was used, and the PCR conditions were 30 cycles of denaturation at 96° C. for 30 seconds, annealing at 53° C. for 30 seconds, and polymerization at 72° C. for 1 minute. As a result, 558 bp of an amplified gene containing the N-terminal region and the linker region of the metB gene and 527 bp of an amplified gene containing the C-terminal region and the linker region of the metB gene were obtained, respectively.

PCR was performed using the two amplified genes obtained above as templates, and the PCR conditions were 10 cycles of denaturation at 96° C. for 60 seconds, annealing at 50° C. for 60 seconds, and polymerization at 72° C. for 1 minute, and then SEQ ID NOS: 12 and 15 were added and the polymerization reaction was further repeated 20 cycles. As a result, 1064 bp of an inactivation cassette containing the N-terminus-linker-C-terminus of the metB gene was obtained.

A pDCM2 vector (SEQ ID NO: 7, Korean Patent Publication No. 10-2020-0136813) was treated with SmaI, and the PCR product (1064 bp) obtained above and the pDCM2 vector treated with SmaI restriction enzyme were subjected to fusion cloning using an Infusion HD cloning kit (In-Fusion® HD Cloning Kit, Clontech). The cloned vector was transformed into *E. coli* DH5α, and the transformed *E. coli* was plated on an LB solid medium containing 25 mg/l of kanamycin. After selecting the colonies transformed with the plasmid from the LB solid medium, the plasmid was obtained using a plasmid extraction method (U.S. Pat. No.

5,981,235 A), and finally, a pDCM2-ΔmetB recombinant vector in which the metB gene deletion cassette was cloned was constructed.

The constructed pDCM2-ΔmetB vector was transformed into the KCCM12634P strain using an electric pulse method, and through a secondary crossover process, KCCM12634PΔmetB was obtained, in which the metB gene was inactivated on the chromosome. The inactivated metB gene was finally confirmed by PCR using primers of SEQ ID NOS: 12 and 15, and then by comparing with ATCC13032, in which the metB gene was not inactivated.

Example 3-2. Preparation of Strain-2

Through PCR using chromosomal DNA of *Corynebacterium glutamicum* ATCC13032 as a template, the metY gene encoding O-acetyl homoserine (thiol)-lyase in the O-acetyl homoserine degradation pathway was obtained. The nucleotide sequence information (NCBI No. Ncgl0625, SEQ ID NO: 16) of the metY gene was obtained from National Institutes of Health (NIH) GenBank, and based on this, primers (SEQ ID NOS: 17 and 18) containing a N-terminal region and a linker region of the metY gene and primers (SEQ ID NOS: 19 and 20) containing a C-terminal region and a linker region were synthesized. Primer sequences are as in Table 6 below.

TABLE 6

| SEQ ID NO. | Sequence name | Sequence |
|---|---|---|
| SEQ ID NO: 17 | metY_N_del F | CCAAAGACAAGGAGACCA |
| SEQ ID NO: 18 | metY_N_del R | AGTCTATTTAAAGcccgggTTGGAGGTCCTTAAGAGTTTT |
| SEQ ID NO: 19 | metY_C_del F | TAAGGACCTCCAAcccgggCTTTAAATAGACTCACCCCAG |
| SEQ ID NO: 20 | metY_C_del R | ATGCCGAGTGCGTCGAGG |

PCR was performed using the chromosomal DNA of ATCC13032 as a template and primers of SEQ ID NOS: 17 and 18 and SEQ ID NOS: 19 and 20. As a polymerase, PfuUltra™ high-fidelity DNA polymerase (Stratagene) was used, and the PCR conditions were 30 cycles of denaturation at 96° C. for 30 seconds, annealing at 53° C. for 30 seconds, and polymerization at 72° C. for 1 minute. As a result, 548 bp of an amplified gene containing the N-terminal region and the linker region of the metY gene and 550 bp of an amplified gene containing the C-terminal region and the linker region of the metY gene were obtained, respectively. PCR was performed using the two amplified genes obtained above as templates, and the PCR conditions were 10 cycles of denaturation at 96° C. for 60 seconds, annealing at 50° C. for 60 seconds, and polymerization at 72° C. for 1 minute, and then SEQ ID NOS: 17 and 20 were added and the polymerization reaction was further repeated 20 cycles. As a result, 1077 bp of an inactivation cassette containing the N-terminus-linker-C-terminus of the metY gene was obtained.

A pDCM2 vector (SEQ ID NO: 7, Korean Patent Publication No. 10-2020-0136813) was treated with SmaI, and the PCR product (1077 bp) obtained above and the pDCM2 vector treated with SmaI restriction enzyme were subjected to fusion cloning using an Infusion HD cloning kit (In-Fusion® HD Cloning Kit, Clontech). The cloned vector was transformed into *E. coli* DH5α, and the transformed *E. coli* was plated on an LB solid medium containing 25 mg/l of kanamycin. After selecting the colonies transformed with the plasmid from the LB solid medium, the plasmid was obtained using a plasmid extraction method (U.S. Pat. No. 5,981,235 A), and finally, a pDCM2-ΔmetY recombinant vector in which the metY gene deletion cassette was cloned was constructed.

The constructed pDCM2-ΔmetY vector was transformed into the strain KCCM12634PΔmetB prepared in Example 3-1 using an electric pulse method, and through a secondary crossover process, KCCM12634P ΔmetB ΔmetY was obtained, in which the metY gene was further inactivated on the chromosome. The inactivated metY gene was finally confirmed by PCR using primers of SEQ ID NOS: 17 and 20, and then by comparing with ATCC13032, in which the metY gene was not inactivated.

Example 3-3. Preparation of Strain-3

In order to introduce a mutation (L377K) (Korean Patent Publication No. 10-2019-0003019) for enhanced expression of lysC gene and for release of feedback inhibition of L-lysine and L-threonine into the lysC gene (SEQ ID NO: 21) encoding aspartokinase derived from *Corynebacterium glutamicum* ATCC13032, and to construct a vector including the mutant lysC gene, a pair of primers (SEQ ID NOS: 22 and 23) for amplifying the 5' upstream region and a pair of primers (SEQ ID NOS: 24 and 25) for amplifying the 3' downstream region, centering around the mutation site, were designed. Primer sequences are as in Table 7 below.

TABLE 7

| SEQ ID NO. | Sequence name | Sequence |
|---|---|---|
| SEQ ID NO: 22 | lysC_L377K_5 F | CAGAAGCTGGAAAAGCTCA |
| SEQ ID NO: 23 | lysC_L377K_5 R | ATCTCAGAGGTGGAAATCttTTCGATGTTCACGTTGACAT |
| SEQ ID NO: 24 | lysC_L377K_3 F | TGTCAACGTGAACATCGAAaaGATTTCCACCTCTGAGATT |
| SEQ ID NO: 25 | lysC_L377K_3 R | TCCTTGTCGGAAGGGTTCA |

PCR was performed using the chromosome of ATCC13032 as a template and primers of SEQ ID NO: 22 and SEQ ID NO: 23, SEQ ID NO: 24 and SEQ ID NO: 25. PCR conditions were denaturation at 95° C. for 5 minutes, and then 30 cycles of denaturation at 95° C. for 30 seconds, annealing at 55° C. for 30 seconds, and polymerization at 72° C. for 30 seconds, followed by polymerization at 72° C. for 7 minutes. As a result, 512 bp of a DNA fragment of the 5' upstream region and 522 bp of a DNA fragment of the 3' downstream region, centering around the mutation site of the lysC gene, were obtained.

PCR was performed using the two amplified DNA fragments as templates and primers of SEQ ID NO: 22 and SEQ ID NO: 25. PCR conditions were denaturation at 95° C. for 5 minutes, and then 30 cycles of denaturation at 95° C. for 30 seconds, annealing at 55° C. for 30 seconds, and polymerization at 72° C. for 60 seconds, followed by polymerization at 72° C. for 7 minutes. As a result, 1011 bp of a DNA fragment was amplified, the DNA fragment including the mutant lysC (L377K) gene encoding the aspartokinase variant, in which leucine at position 377 was substituted with lysine.

A pDCM2 vector (SEQ ID NO: 7, Korean Patent Publication No. 10-2020-0136813) was treated with SmaI, and the PCR product (1011 bp) obtained above and the pDCM2 vector treated with SmaI restriction enzyme were subjected to fusion cloning using an Infusion HD cloning kit (In-Fusion® HD Cloning Kit, Clontech). The cloned vector was transformed into *E. coli* DH5α, and the transformed *E. coli* was plated on an LB solid medium containing 25 mg/l of kanamycin. After selecting the colonies transformed with the plasmid from the LB solid medium, the plasmid was obtained using a plasmid extraction method (U.S. Pat. No. 5,981,235 A), and finally, a pDCM2-lysC (L377K) recombinant vector was constructed, in which the lysC (L377K) gene-substituted cassette was cloned.

The constructed pDCM2-lysC (L377K) vector was transformed into the KCCM12634P ΔmetB ΔmetY strain prepared in Example 3-2 using an electric pulse method, and through a secondary crossover process, *Corynebacterium glutamicum* KCCM12634P ΔmetB ΔmetY lysC (L377K) was obtained, in which the nucleotide mutation was introduced into the lysC gene on the chromosome. The nucleotide mutation-introduced gene was finally confirmed by PCR using primers of SEQ ID NOS: 22 and 25, and then by comparing with the sequence of the wild-type lysC gene through sequencing.

Example 3-4. Preparation of Endogenous Gene NCgl0959-Deleted Strain-1

In order to maximize O-acetyl homoserine production, the pDCM2-ΔNCgl0959 vector constructed in Example 1-1 was transformed into the KCCM12634P ΔmetB ΔmetY lysC (L377K) strain prepared in Example 3-3 using the electric pulse method, and then through a secondary crossover process, KCCM12634P ΔmetB ΔmetY lysC (L377K) ΔNCgl0959 was obtained, in which the NCgl0959 gene was deleted on the chromosome. The inactivation of the NCgl0959 gene was finally confirmed by PCR using primers of SEQ ID NOS: 8 and 9, and then by comparing with ATCC13032, in which the NCgl0959 gene was not inactivated.

Example 3-5. Preparation of Endogenous Gene NCgl0959-Deleted Strain-2

To amplify the gene encoding homoserine acetyl transferase (MetX), the nucleotide sequence information (NCBI No. NCgl0624, SEQ ID NO: 26) of the metX gene was obtained from National Institutes of Health (NIH) GenBank, and based on this, a pair of primers (SEQ ID NO: 27 and 28) for amplification from the promoter region (about 300 bp upstream the start codon) to the terminator region (about 100 bp downstream the stop codon) were designed by inserting BamHI restriction enzyme sites at both ends. PCR conditions were denaturation at 95° C. for 5 minutes, and then 30 cycles of denaturation at 95° C. for 30 seconds, annealing at 55° C. for 30 seconds, and polymerization at 72° C. for 90 seconds, followed by polymerization at 72° C. for 7 minutes. As a result, 1546 bp of a DNA fragment of the coding region of the metX gene was obtained. The pECCG117 (KR 10-0057684) vector and the metX DNA fragment were treated with the restriction enzyme BamHI, and ligated using DNA ligase. Then, cloning was performed to obtain a plasmid, which was named pECCG117-metX WT. Primer sequences are as in Table 8 below.

TABLE 8

| SEQ ID NO. | Sequence name | Sequence |
|---|---|---|
| SEQ ID NO: 27 | metX F | GGATCCCCTCGTTGTTCACCCAGCAACC |
| SEQ ID NO: 28 | metX R | GGATCCCAAAGTCACAACTACTTATGTTAG |

The constructed pECCG117-metX WT vector was introduced into the KCCM12634P ΔmetB ΔmetY lysC (L377K) strain prepared in 3-3 and the KCCM12634P ΔmetB ΔmetY lysC (L377K) ΔNCgl0959 strain prepared in Example 3-4 by an electric pulse method, respectively, and then each was plated on an LB solid medium containing 25 mg/l of kanamycin to obtain transformants, KCCM12634P ΔmetB ΔmetY lysC (L377K)/pECCG117-metX WT and KCCM12634P ΔmetB ΔmetY lysC (L377K) ΔNCgl0959/pECCG117-metX WT.

Example 3-6. Evaluation of O-Acetyl Homoserine-Producing Ability

To compare the O-acetyl homoserine-producing ability between the strains prepared in Examples 3-3 to 3-5, they were cultured in the following manner and O-acetyl homoserine in the culture medium was analyzed.

One platinum loop of each strain was inoculated into a 250 ml corner-baffled flask containing 25 ml of the following medium, and cultured at 33° C. for 20 hours with shaking at 200 rpm. The concentration of O-acetyl homoserine was analyzed using HPLC, and the analyzed concentration was as in Table 9.

<O-Acetyl Homoserine Production Medium (pH 7.2)>

30 g of glucose, 2 g of $KH_2PO_4$, 3 g of urea, 40 g of $(NH_4)_2SO_4$, 2.5 g of peptone, 5 g (10 ml) of CSL (Sigma), 0.5 g of $MgSO_4 \cdot 7H_2O$, 400 mg of methionine, 20 g of $CaCO_3$ (based on 1 liter of distilled water)

TABLE 9

| Strains | O—AH (g/L) |
|---|---|
| KCCM12634P ΔmetB ΔmetY lysC(L377K) | 1.30 |
| KCCM12634P ΔmetB ΔmetY lysC(L377K)ΔNCgl0959 | 1.69 |
| KCCM12634P ΔmetB ΔmetY lysC(L377K) /pECCG117-metX WT | 2.10 |
| KCCM12634P ΔmetB ΔmetY lysC(L377K)ΔNCgl0959 /pECCG117-metX WT | 2.73 |

As a result, as shown in Table 9, when the control strain KCCM12634P ΔmetB ΔmetY lysC (L377K) was cultured, 1.3 g/L of O-acetyl homoserine was accumulated, and when KCCM12634P ΔmetB ΔmetY lysC (L377K) ΔNCgl0959 was cultured, 1.69 g/L of O-acetyl homoserine was accumulated, indicating about 130% production ability, relative to that of the control group. In addition, when the KCCM12634P ΔmetB ΔmetY lysC (L377K)/pECCG117-metX WT strain was cultured, 2.10 g/L of O-acetyl homoserine was accumulated, and when the KCCM12634P ΔmetB ΔmetY lysC (L377K) ΔNCgl0959/pECCG117-metX WT was cultured, 2.73 g/L of O-acetyl homoserine was accumulated, indicating about 130% production ability, relative to that of the KCCM12634P ΔmetB ΔmetY lysC (L377K)/pECCG117-metX WT strain.

Accordingly, it was confirmed that the production ability of the desired amino acid may be further improved when the endogenous gene NCgl0959 is deleted and inactivated in the strain with increased O-acetyl-L homoserine-producing ability.

Based on the above description, it will be understood by those skilled in the art that the present disclosure may be implemented in a different specific form without changing the technical spirit or essential characteristics thereof. In this regard, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

The invention claimed is:

1. A microorganism of the genus *Corynebacterium* with an O-acetyl homoserine-producing ability, wherein activity of a GNAT family N-acetyltransferase protein is weakened.

2. The microorganism of the genus *Corynebacterium* of claim 1, wherein the microorganism of the genus *Corynebacterium* is *Corynebacterium glutamicum.*

3. The microorganism of the genus *Corynebacterium* of claim 1, wherein the GNAT family N-acetyltransferase is a protein consisting of an amino acid sequence of SEQ ID NO: 1.

4. The microorganism of the genus *Corynebacterium* of claim 1, wherein the weakening is inactivating.

5. The microorganism of the genus *Corynebacterium* of claim 1, wherein a nucleotide sequence of SEQ ID NO: 2 is deleted.

6. The microorganism of the genus *Corynebacterium* of claim 1, wherein activity of an L-methionine/branched-chain amino acid exporter YjeH protein is further enhanced.

7. The microorganism of the genus *Corynebacterium* of claim 6, wherein an amino acid sequence of SEQ ID NO: 10 is introduced.

8. A method for producing O-acetyl homoserine, the method comprising the step of culturing, in a medium, a microorganism of the genus *Corynebacterium* with an O-acetyl homoserine-producing ability, wherein activity of a GNAT family N-acetyltransferase protein is weakened.

9. A method for producing L-methionine, the method comprising the steps of:

culturing, in a medium, a microorganism of the genus *Corynebacterium* with an O-acetyl homoserine-producing ability, wherein activity of a GNAT family N-acetyltransferase protein is weakened;

producing O-acetyl homoserine from the cultured microorganism or the medium; and converting the O-acetyl homoserine into L-methionine.

* * * * *